(12) United States Patent
Koch et al.

(10) Patent No.: US 7,276,512 B2
(45) Date of Patent: Oct. 2, 2007

(54) BENZO[A]PYRANO[3,2-H]ACRIDIN-7-ONE COMPOUNDS

(75) Inventors: Michel Koch, La Celle Saint Cloud (FR); François Tillequin, Paris (FR); Sylvie Michel, Paris (FR); John Hickman, Paris (FR); Alain Pierre, Les Alluets Le Roi (FR); Stéphane Leonce, Versailles (FR); Bruno Pfeiffer, Saint Leu La Foret (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 221 days.

(21) Appl. No.: 10/872,060

(22) Filed: Jun. 18, 2004

(65) Prior Publication Data

US 2004/0266753 A1    Dec. 30, 2004

(30) Foreign Application Priority Data

Jun. 25, 2003    (FR) .................................. 03 07664

(51) Int. Cl.
*A61K 31/44*    (2006.01)
(52) U.S. Cl. ..................................... 514/280
(58) Field of Classification Search ................. 514/283
See application file for complete search history.

(56) References Cited

OTHER PUBLICATIONS

Goodman &Gilman's, The Pharmacological Basis of Therapeutics, Ninth Edition, (1996), Calabresi et al., Section X, Chemotherapy of Neoplastic Diseases, pp. 1225-1232.*
Gura, T. Systems for identifying new drugs are often faulty, Science, 1997, 278:1041-1042.*
Johnson et al. Relationships between drug activity in NCI preclinical in vitro and in vivo models and early clinical trials. British J. of Cancer, 2001, 84(10):1424-1431.*
Elomri et al. Synthesis and cytotoxic and antitumor activity of esters in the 1,2-dihydroxy-1,2-dihydroacronycine series. J. Med. Chem., 1996, vol. 39, pp. 4762-4766.*

* cited by examiner

Primary Examiner—Phyllis G. Spivack
Assistant Examiner—James D. Anderson
(74) Attorney, Agent, or Firm—Hueschen and Sage

(57) ABSTRACT

A compound selected from those of formula (I):

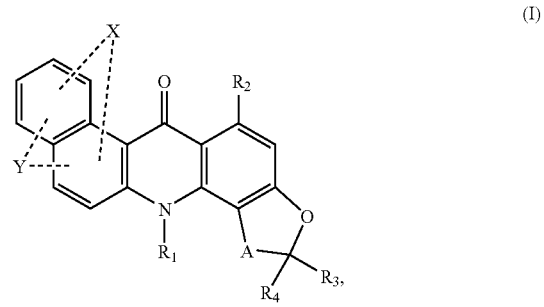

(I)

wherein:
X and Y represent a group selected from hydrogen, halogen, hydroxy, alkoxy, nitro, cyano, alkyl, trihaloalkyl and $NR_aR_b$, wherein $R_a$ and $R_b$ are as defined in the description $R_1$ represents hydrogen or alkyl $R_2$ represents a group selected from hydrogen, alkyl, $-OR''_a$, $-NR'_aR'_b$, $-O-T_a-OR''_a$, $-NR''_a-T_a-NR'_aR'_b$, $-NR''_a-C(O)-T_aH$, $-O-C(O)-T_aH$, $-O-T_a-NR'_aR'_b$, $-NR''_a-T_a-OR''_a$, $-NR''-T_a-CO_2R''_a$ and $-NR''_a-C(O)-T_a-NR'_aR'_b$, wherein $R'_a$, $R''_a$, $R'_b$ and $T_a$ are as defined in the description $R_3$ and $R_4$ represent hydrogen or alkyl A represents a group of formula $-CH(R_5)-CH(R_6)-$, $-CH=C(R_7)-$, $-C(R_7)=CH-$, $-C(O)-CH(R_8)$ or $-CH(R_8)-C(O)$, wherein $R_5$, $R_6$, $R_7$ and $R_8$ are as defined in the description its isomers, N-oxides, and addition salts thereof with a pharmaceutically acceptable acid or base, and medicinal products containing the same which are useful in the treatment of cancer.

19 Claims, No Drawings

BENZO[A]PYRANO[3,2-H]ACRIDIN-7-ONE COMPOUNDS

The present invention relates to new benzo[α]pyrano[3,2-h]acridin-7-one compounds.

FIELD OF THE INVENTION

The compounds of the invention are derivatives of acronycine, an alkaloid which has anti-tumour properties that have been demonstrated in experimental models (*J. Pharm. Sci.*, 1966, 55 (8), 758-768). However, despite having quite a broad spectrum of activity, acronycine is of low potency and moderate activity. The solubility of the compound is, moreover, low, which limits its bioavailability, as well as its use in pharmaceutical compositions for administration by the intravenous route.

Various modifications have been made to the molecule, for example those described in *J. Med. Chem.*, 1996, 39, 4762-4766 or EP 1 042 326, allowing a significant improvement in the potency, anti-tumour efficacy and solubility of the products. Nevertheless, anti-cancer therapeutic requirements call for the constant development of new anti-tumour agents with the aim of obtaining medicaments that are simultaneously more active and better tolerated. More specifically, solid tumours constitute a major problem for anti-cancer chemotherapy because of their intrinsic and/or acquired resistance to existing compounds. It is therefore of prime importance to have access to the widest possible range of compounds exhibiting powerful cytotoxic activity in order to have available the most effective treatments for the totality of tumour disorders.

Besides the fact that the compounds of the invention are new, they have surprising in vitro and in vivo cytotoxic activity which is greater than that observed hitherto. The compounds discovered by the Applicant accordingly have anti-tumour properties that make them especially useful in the treatment of cancers. Among the types of cancer which may be treated by the compounds of the present invention there may be mentioned, without implying any limitation, adenocarcinonmas and carcinomas, sarcomas, gliomas and leukaemias.

DETAILED DESCRIPTION OF THE INVENTION

More specifically, the present invention relates to compounds of formula (I):

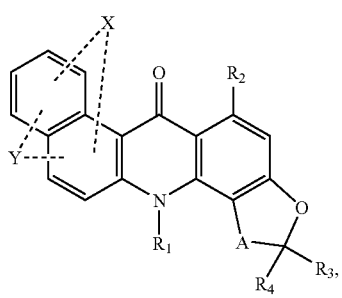

(I)

wherein:
X and Y, which may be the same or different, represent, each independently of the other, a group selected from:
hydrogen and halogen atoms,
hydroxy, linear or branched $(C_1-C_6)$alkoxy, nitro, cyano, linear or branched $(C_1-C_6)$alkyl, linear or branched $(C_2-C_6)$alkenyl and linear or branched $(C_1-C_6)$polyhaloalkyl groups and
a group of formula —$NR_aR_b$, wherein:
   $R_a$ and $R_b$, which may be the same or different, represent, each independently of the other, a group selected from a hydrogen atom, —C(O)—$CF_3$, —C(O)—$NH_2$ and a linear or branched $(C_1-C_6)$alkyl group optionally substituted by a group $NR'_aR'_b$, wherein:
      $R'_a$ and $R'_b$, which may be the same or different, represent, each independently of the other, a group selected from a hydrogen atom, a linear or branched $(C_1-C_6)$alkyl group, an aryl group and an aryl-$(C_1-C_6)$alkyl group in which the alkyl moiety is linear or branched, or $R'_a$ and $R'_b$, together with the nitrogen atom carrying them, form a monocyclic, 5- to 7-membered heterocycle optionally containing within the cyclic system a second hetero atom selected from oxygen and nitrogen,
   or $R_a$ and $R_b$, together with the nitrogen atom carrying them, form a monocyclic, 5- to 7-membered heterocycle optionally containing within the cyclic system a second hetero atom selected from oxygen and nitrogen,
   it being understood that the substituents X and Y may be present on either of the two adjacent benzene rings,
$R_1$ represents a hydrogen atom or a linear or branched $(C_1-C_6)$alkyl group,
$R_2$ represents a group selected from a hydrogen atom and linear or branched $(C_1-C_6)$alkyl; —$OR''_a$; —$NR'_aR'_b$; —O-$T_a$-$OR''_a$; —$NR''_a$-$T_a$-$NR'_aR'_b$; —$NR''_a$—C(O)-$T_aH$; —O—C(O)-$T_aH$; —O-$T_a$-$NR'_aR'_b$; —$NR''_a$-$T_a$-$OR''_a$; —$NR''_a$-$T_a$-$CO_2R''_a$; and —$NR''_a$—C(O)-$T_a$-$NR'_aR'_b$ groups,
wherein
$T_a$ represents a linear or branched $(C_1-C_6)$alkylene chain,
$R'_a$ and $R'_b$ are as defined hereinbefore,
$R''_a$ represents a group selected from a hydrogen atom and a linear or branched $(C_1-C_6)$alkyl group,
$R_3$ and $R_4$, which may be the same or different, represent, each independently of the other, a hydrogen atom or a linear or branched $(C_1-C_6)$alkyl group, or $R_3$ and $R_4$, together with the carbon atom carrying them, form a monocyclic, 3- to 6-membered cyclic group,
A represents a group of formula:

—CH($R_5$)—CH($R_6$)—, a)

wherein:
$R_5$ and $R_6$, which may be the same or different, represent, each independently of the other, a group selected from:
1) a hydrogen atom,
2) $OR_c$, $NR_cR_d$ and $SR_c$ groups, wherein:
   $R_c$ and $R_d$, which may be the same or different, represent, each independently of the other, a group selected from a hydrogen atom, a linear or branched $(C_1-C_6)$alkyl group, an aryl group and an aryl-$(C_1-C_6)$alkyl group in which the alkyl moiety is linear or branched, and a C(O)—$R_e$ group, wherein $R_e$ represents a group selected from a hydrogen atom, an aryl group and an $NR'''_aR'''_b$ group, wherein $R'''_a$ and $R'''_b$, which may be the same or different, each represent a hydrogen atom or a linear or branched $(C_1-C_6)$alkyl group, or $R'''_a$ and $R'''_b$, together with the nitrogen atom carrying them, form a monocyclic, 5- to 7-membered heterocycle optionally containing within the cyclic system a second hetero atom selected from oxygen and nitrogen, 3) $W_1$—$C(W_2)$—U—V, wherein:
   α) $W_1$ represents an oxygen atom, a sulphur atom or $NR_c$ (wherein $R_c$ is as defined hereinbefore),
   β) $W_2$ represents an oxygen atom or a sulphur atom,
   γ) U represents a linear or branched ($C_1$-$C_8$)alkylene chain or a linear or branched ($C_2$-$C_8$)alkenylene chain,
   δ) V represents a group selected from:
      a hydrogen atom,
      an aryl group,
      $OR_c$, $CO_2R_c$, $COR_c$, $CONR'_aR'_b$, $NR'_aR'_b$, $N(R_c)$—$CO_2R'_c$ and $N(R_c)$—$COR'_c$ groups, wherein $R'_a$, $R'_b$ and $R_c$ are as defined hereinbefore and $R'_c$ represents a group selected from a hydrogen atom, a linear or branched ($C_1$-$C_6$)alkyl group, an aryl group and an aryl-($C_1$-$C_6$)alkyl group in which the alkyl moiety is linear or branched,
   ε) U represents a bond when $W_2$ does not represent an oxygen atom and when simultaneously V does not represent a group selected from:
      a hydrogen atom,
      an aryl group,
      $NH_2$, 4) $W_1$—$C(W_2)$—$W_3$-$T_1$, wherein:
   α) $W_1$ and $W_2$ are as defined hereinbefore,
   δ) $W_3$ represents an oxygen atom, a sulphur atom or $NR_c$ wherein $R_c$ is as defined hereinbefore,
   γ) $T_1$ represents a group selected from:
      a hydrogen atom,
      linear or branched ($C_1$-$C_6$)alkyl,
      linear or branched ($C_2$-$C_6$)alkenyl,
      aryl, aryl-($C_1$-$C_6$)alkyl in which the alkyl moiety is linear or branched,
      a linear or branched ($C_1$-$C_6$)alkylene chain and a linear or branched ($C_2$-$C_6$)alkenylene chain, each being substituted by an $OR_c$ group, wherein $R_c$ is as defined hereinbefore, or by $NR'_aR'_b$, wherein $R'_a$ and $R'_b$ are as defined hereinbefore, 5) $W_1$—$S(O)_n$—$W_3$-$T_1$, wherein:
   α) $W_1$, $W_3$ and $T_1$ are as defined hereinbefore,
   β) n represents an integer selected from 1 and 2, 6) $W_1$—$S(O)_n$—U'—V', wherein:
   α) U' represents a linear or branched ($C_1$-$C_8$)alkylene chain or a linear or branched ($C_2$-$C_8$)alkenylene chain,
   β) V' represents a group selected from:
      a hydrogen atom,
      an aryl group,
      $OR_c$, $CO_2R_c$, $COR_c$, $CONR'_aR'_b$, $NR'_aR'_b$, $N(R_c)$—$CO_2R'_c$ and $N(R_c)$—$COR'_c$ groups, wherein $R'_a$, $R'_b$, $R_c$ and $R'_c$ are as defined hereinbefore, and
   γ) $W_1$ and n are as defined hereinbefore, 7) $C(W_2)$-$T_1$, wherein $W_2$ and $T_1$ are as defined hereinbefore, or $R_5$ and $R_6$ together form:
1) a group

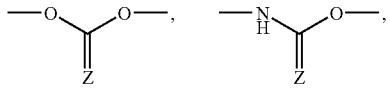, 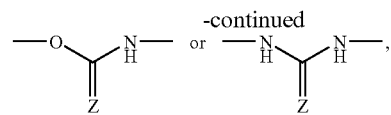

-continued

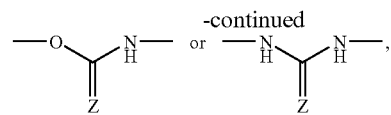

wherein Z represents an oxygen atom or a sulphur atom, 2) a group —O—$(CH_2)_m$—O—, wherein m represents an integer of from 1 to 4 inclusive, 3) a group

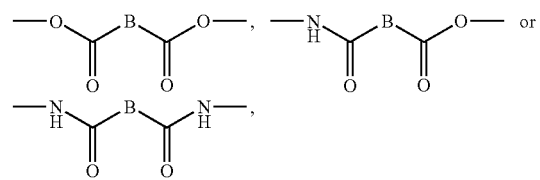

wherein B represents a single bond, a linear or branched ($C_1$-$C_6$)alkylene chain or a linear or branched ($C_2$-$C_6$)alkenylene chain, or $R_5$ and $R_6$, together with the carbon atoms carrying them, form an oxirane group or an aziridine group optionally substituted on the nitrogen atom by a linear or branched ($C_1$-$C_6$)alkyl group, b) —CH=C($R_7$)— or —C($R_7$)=CH—, wherein $R_7$ represents a group selected from:
a hydrogen atom,
$OR''_a$, $W_1$—$C(W_2)$—U—V, $W_1$—$C(W_2)$—$W_3$-$T_1$, $W_1$—$S(O)_n$—$W_3$-$T_1$, $W_1$—$S(O)_n$—U'—V', and $C(W_2)$-$T_1$ groups, wherein $R''_a$, $W_1$, $W_2$, $W_3$, U, V, U', V', $T_1$ and n are as defined hereinbefore, or c) —C(O)—CH($R_8$)— or —CH($R_8$)—C(O)—, wherein $R_8$ represents a group selected from:
a hydrogen atom,
linear or branched ($C_1$-$C_6$)alkyl-carbonyloxy and an $OR''_a$ group, wherein $R'_a$ is as defined hereinbefore, to their enantiomers, diastereoisomers and N-oxides, and to addition salts thereof with a pharmaceutically acceptable acid or base, aryl being understood to mean a phenyl or naphthyl group optionally containing one or more, identical or different, substituents selected from hydroxy, halogen, carboxy, nitro, amino, linear or branched ($C_1$-$C_6$)alkylamino, di($C_1$-$C_6$)alkylamino wherein each alkyl moiety may be linear or branched, linear or branched ($C_1$-$C_6$)alkoxy, linear or branched ($C_1$-$C_6$)acyl and linear or branched ($C_1$-$C_6$)alkyl-carbonyloxy.

Among the monocyclic, 5- to 7-membered heterocycle optionally containing within the cyclic system a second hetero atom selected from oxygen and nitrogen, there may be mentioned by way of non-limiting example the groups pyrrolidyl, isoxazolidyl, oxazolidyl, pyrazolidyl, imidazolyl, piperidyl, oxazinyl, morpholyl, hexahydropyridazyl, hexahydropyrimidyl, piperazyl, azepanyl, oxazepanyl, diazepanyl.

Among the monocyclic, 3- to 6-membered cyclic group, there may be mentioned by way of non-limiting example the groups cyclopropyl, cyclobutyl, cyclopentyl and cyclohexyl.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, lysine etc.

Among the pharmaceutically acceptable bases there may be mentioned, without implying any limitation, sodium hydroxide, potassium hydroxide, triethylamine, tert-butylamine etc.

According to an advantageous embodiment of the invention, preferred compounds are compounds of formula (IA):

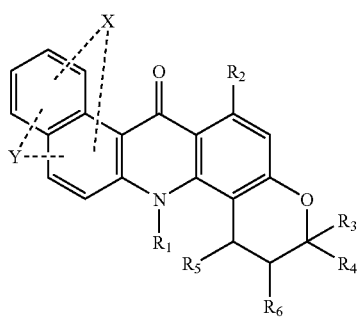

(IA)

wherein X, Y, $R_1$, $R_2$, $R_3$, $R_4$, $R_5$ and $R_6$ are as defined for formula (I).

Preferred compounds of formula (IA) are compounds wherein $R_5$ and $R_6$, which may be the same or different, each represent a group of formula —$OR_c$, $W_1$—$C(W_2)$—U—V, $W_1$—$C(W_2)$—$W_3$-$T_1$, $C(W_2)$-$T_1$ or $R_5$ and $R_6$ together form a group

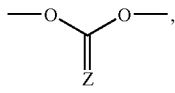

wherein $R_c$, $W_1$, $W_2$, $W_3$, U, V, $T_1$ and Z are as defined for formula (I).

In especially interesting manner, preferred compounds of formula (IA) are compounds wherein $R_5$ and $R_6$ are identical and each represent a group of formula —$OR_c$, wherein $R_c$ represents a hydrogen atom.

In another especially interesting manner, preferred compounds of formula (IA) are compounds wherein $R_5$ and $R_6$, which may be the same or different, each represent a group of formula $W_1$—$C(W_2)$—U—V, wherein $W_1$ and $W_2$ each represent an oxygen atom, U is as defined for formula (I) and V represents a hydrogen atom or U represents a linear or branched ($C_1$-$C_8$)alkylene chain and V represents a group NR'$_a$R'$_b$, wherein R'$_a$ and R'$_b$, which may be the same or different, each represent a hydrogen atom or a linear or branched ($C_1$-$C_6$)alkyl group.

In even more interesting manner, preferred compounds of formula (IA) are compounds wherein $R_5$ represents a group of formula —$OR_c$, wherein $R_c$ represents a hydrogen atom, and $R_6$ represents a group of formula $W_1$—$C(W_2)$—U—V, wherein $W_1$ and $W_2$ each represent an oxygen atom, U represents a linear or branched ($C_1$-$C_8$)alkylene chain and V represents a hydrogen atom.

In an other even more interesting manner, preferred compounds of formula (IA) are compounds wherein $R_5$ represents a group of formula —$OR_c$, or $W_1$—$C(W_2)$—U—V, wherein $R_c$ represents a hydrogen atom, $W_1$ and $W_2$ each represent an oxygen atom, U represents a linear or branched ($C_1$-$C_8$)alkylene chain and V represents a hydrogen atom, and $R_6$ represents a group of formula $W_1$—$C(W_2)$—U—V, wherein $W_1$ and $W_2$ each represent an oxygen atom, U represents a linear or branched ($C_2$-$C_8$)alkenylene chain and V represents a hydrogen atom or an aryl group.

In interesting manner, preferred compounds of formula (IA) are compounds wherein $R_5$ and $R_6$, which may be the same or different, each represent a group of formula $W_1$—$C(W_2)$—$W_3$-$T_1$, wherein $W_1$ and $W_2$ each represent an oxygen atom, $W_3$ represents a group —$NR_C$, wherein $R_c$ represents a linear or branched ($C_1$-$C_6$)alkyl group, and $T_1$ represents a linear or branched ($C_1$-$C_6$)alkyl group.

In another very interesting manner, preferred compounds of formula (IA) are compounds wherein $R_5$ and $R_6$ together form a group

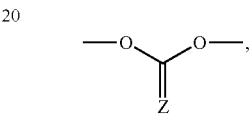

wherein Z represents an oxygen atom.

According to a second advantageous embodiment of the invention, preferred compounds are compounds of formula (IB):

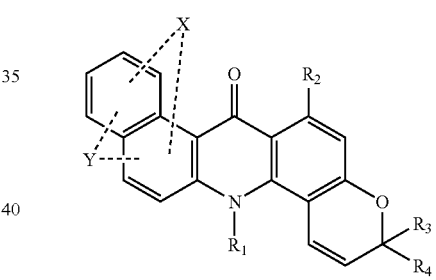

(IB)

wherein X, Y, $R_1$, $R_2$, $R_3$ and $R_4$ are as defined for formula (I).

Substituents $R_3$ and $R_4$ that are preferred according to the invention are linear or branched ($C_1$-$C_6$)alkyl groups.

Even more preferably, substituents $R_3$ and $R_4$ that are preferred according to the invention are a methyl group.

Substituents $R_2$ that are preferred according to the invention are —$OR''_a$ and —$NR''_a$-$T_a$-$NR'_aR'_b$ groups, wherein R'$_a$, R'$_b$, R''$_a$ and $T_a$ are as defined for formula (I).

Even more preferably, substituents $R_2$ that are preferred according to the invention are the group —$OR''_a$, wherein R'$_a$ is as defined for formula (I), and the group —$NR''_a$-$T_a$-$NR'_aR'_b$, wherein R''$_a$ represents a hydrogen atom, $T_a$ is as defined for formula (I), and R'$_a$ and R'$_b$, which may be the same or different, each, represent a linear or branched ($C_1$-$C_6$)alkyl group.

Substituents X and Y that are preferred according to the invention are hydrogen atoms.

In especially advantageous manner, preferred compounds of the invention are:

(±)-cis-1,2-dihydroxy-6-methoxy-3,3,14-trimethyl-1,2,3, 14-tetrahydro-7H-benzo[α]-pyrano[3,2-h]acridin-7-one, (±)-cis-1,2-diacetoxy-6-methoxy-3,3,14-trimethyl-1,2,3,14-tetrahydro-7H-benzo[α]-pyrano[3,2-h]acridin-7-one, (±)-cis-7-methoxy-4,4,15-trimethyl-15,15c-dihydro-4H-benzo[α][1,3]dioxolo[4',5':4,5]-pyrano[3,2-h]acridine-2,8(3aH)-dione, 6-methoxy-3,3,14-trimethyl-3,14-dihydro-7H-benzo[α]pyrano[3,2-h]acridin-7-one, 6-hydroxy-3,3,14-trimethyl-3,14-dihydro-7H-benzo[α]pyrano[3,2-h]acridin-7-one, 6-hydroxy-3,3-dimethyl-3,14-dihydro-7H-benzo[α]pyrano[3,2-h]acridin-7-one.

The enantiomers, diastereoisomers, N-oxides and addition salts with a pharmaceutically acceptable acid or base of the preferred compounds form an integral part of the invention.

The present invention relates also to a process for the preparation of compounds of formula (I), which process is characterised in that there is used as starting material a compound of formula (II):

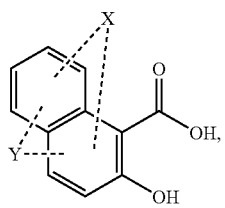

(II)

wherein X and Y are as defined for formula (I), which compound of formula (II) is treated with dimethyl sulphate in a basic medium to yield the compounds of formula (III):

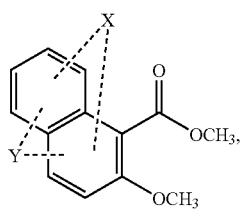

(III)

wherein X and Y are as defined hereinbefore, which compound of formula (III) is treated with Claisen's alkali solution (a solution of potassium hydroxide in a water-methanol mixture) and then with a solution of hydrochloric acid to yield the compounds of formula (IV):

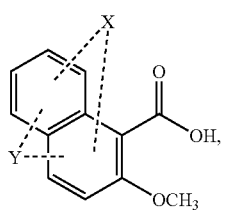

(IV)

wherein X and Y are as defined hereinbefore, which compound of formula (IV) is treated with thionyl chloride and then, in an anhydrous medium, with a compound of formula (V):

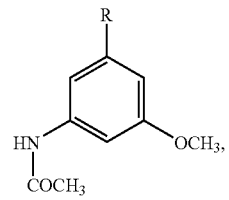

(V)

wherein R represents a hydrogen atom, a hydroxy group, a linear or branched $(C_1$-$C_6)$alkyl group or a linear or branched $(C_1$-$C_6)$alkoxy group, to yield the compounds of formula (VI):

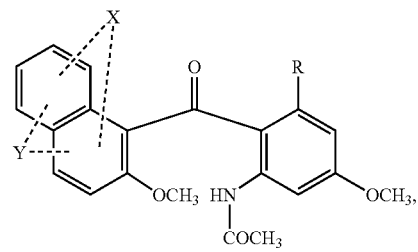

(VI)

wherein X, Y and R are as defined hereinbefore, which compound of formula (VI) is treated with a suspension of sodium hydride in an anhydrous aprotic solvent to yield the compounds of formula (VII):

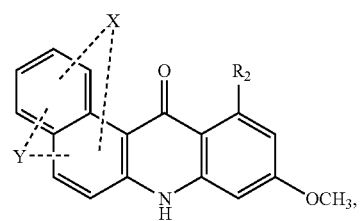

(VII)

wherein X, Y and R are as defined hereinbefore, which compound of formula (VII) is treated with an aqueous solution of hydrobromic acid in acetic acid to yield the compounds of formula (VIII):

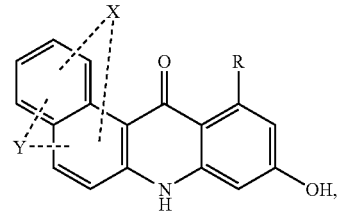

(VIII)

wherein X, Y and R are as defined hereinbefore, which compound of formula (VIII) is then treated under basic conditions in an anhydrous aprotic solvent with an alkyne of formula (IX):

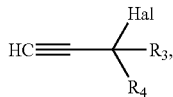
(IX)

wherein Hal represents a halogen atom, and $R_3$ and $R_4$ are as defined for formula (I), to yield the compounds of formula (I/a), a particular case of the compounds of formula (I):

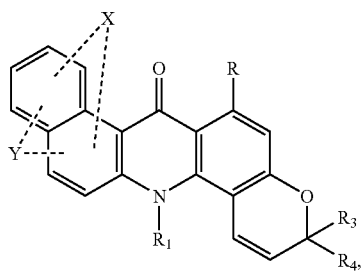
(I/a)

wherein X, Y, R, $R_3$ and $R_4$ are as defined hereinbefore, the nitrogen atom of which compound of formula (I/a) is, if desired substituted by the action of an alkyl halide or of a dialkyl sulphate in the presence of a deprotonating agent, in a polar aprotic solvent, to yield the compounds of formula (I/b), a particular case of the compounds of formula (I):

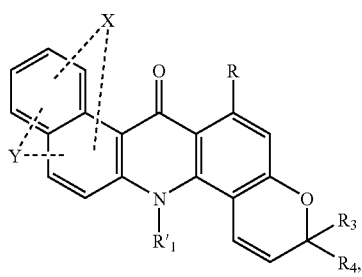
(I/b)

wherein $R'_1$, represents a linear or branched $(C_1-C_6)$alkyl group and X, Y, R, $R_3$ and $R_4$ are as defined hereinbefore, which compounds of formula (I/b), when R represents a hydroxy group, are, if desired subjected to the action of an alkylating agent or acylating agent to yield the compounds of formula (I/c), a particular case of the compounds of formula (I):

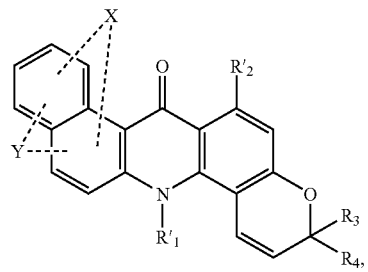
(I/c)

wherein $R'_2$ represents a group selected from $—OR''_a$, $—O-T_a-OR''_a$, $—O—C(O)-T_aH$ and $—O-T_a-NR'_aR'_b$, wherein $R''_a$, $R'_a$; $R'_b$ and $T_a$ are as defined for formula (I), and X, Y, $R'_1$, $R_3$ and $R_4$ are as defined hereinbefore, which compounds of formula (I/c), when $R'_2$ represents a linear or branched $(C_1-C_6)$alkoxy group, are, if desired treated with a compound of formula (X):

$HNR_{10}R_{11}$ (X), wherein $R_{10}$ represents a group selected from $R'_a$ and $R'_a$ which are as defined for formula (I) and $R_{11}$ represents a group selected from $R'_b$, $T_a-NR'_aR'_b$, $—C(O)-T_aH$, $-T_a-OR''_a$ and $-T_a-CO_2R''_a$, wherein $T_a$, $R'_a$, $R'_b$ and $R''_a$ are as defined hereinbefore, to yield the compounds of formula (I/d), a particular case of the compounds of formula (I):

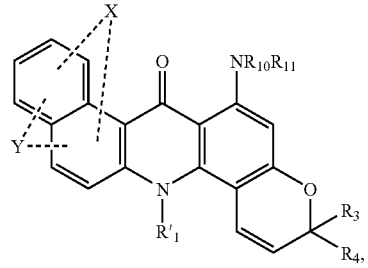
(I/d)

wherein X, Y, $R'_1$, $R_3$, $R_4$, $R_{10}$ and $R_{11}$ are as defined hereinbefore,
the totality of the compounds of formulae (I/a) to (I/d) constituting the compounds of formula (I/e):

(I/e)

wherein X, Y, $R_1$, $R_2$, $R_3$ and $R_4$ are as defined for formula (I),

Which Compounds of Formula (I/e) may be Subjected a) to the action of a reducing agent to yield the compounds of formula (I/f), a particular case of the compounds of formula (I):

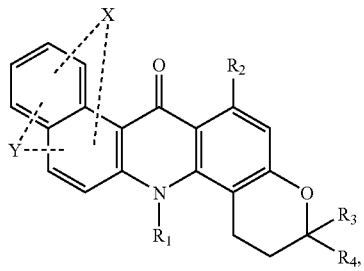
(I/f)

wherein X, Y, $R_1$, $R_2$, $R_3$ and $R_4$ are as defined hereinbefore, b) or to the action of osmium tetroxide in a polar medium and in the presence of 4-methylmorpholine N-oxide to yield the compounds of formulae (I/g$_1$) and (I/g$_2$), a particular case of the compounds of formula (I):

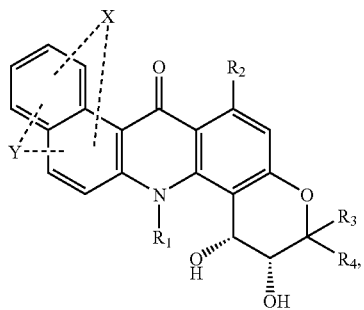
(I/g$_1$)

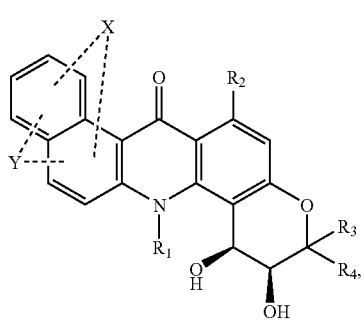
(I/g$_2$)

wherein X, Y, $R_1$, $R_2$, $R_3$ and $R_4$ are as defined hereinbefore, the totality of the compounds of formulae (I/g$_1$) and (I/g$_2$) constituting the cis-diol compounds of formula (cis-I/g):

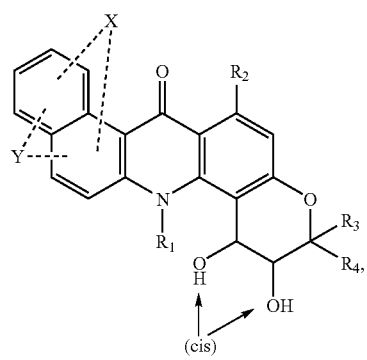
(cis-I/g)

wherein X, Y, $R_1$, $R_2$, $R_3$ and $R_4$ are as defined hereinbefore, which cis-diol compounds of formula (cis-I/g) are, if desired, subjected to the action of a compound of formula (XI):

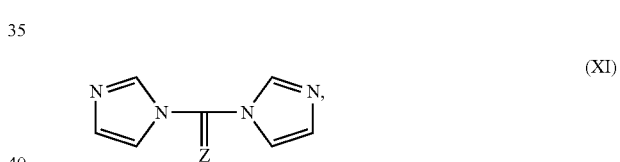
(XI)

wherein Z is as defined for formula (I), to yield the compounds of formula (cis-I/h), a particular case of the compounds of formula (I):

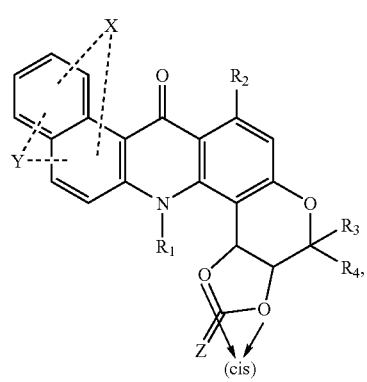
(cis-I/h)

wherein X, Y, $R_1$, $R_2$, $R_3$ and $R_4$ are as defined hereinbefore, c) or to the action of potassium permanganate in a polar medium to yield the compounds of formula (I/i), a particular case of the compounds of formula (I):

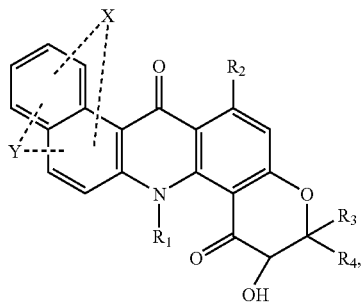
(I/i)

wherein X, Y, R$_1$, R$_2$, R$_3$ and R$_4$ are as defined hereinbefore,

It Being Possible for the Compounds of Formula (I/i) to be Subjected

α) to the action of an alkylating agent or acylating agent to yield the compounds of formula (I/j), a particular case of the compounds of formula (I):

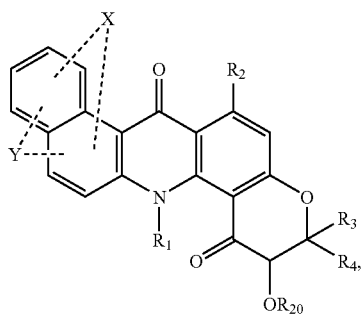
(I/j)

wherein X, Y, R$_1$, R$_2$, R$_3$ and R$_4$ are as defined hereinbefore and R$_{20}$ represents a group selected from linear or branched (C$_1$-C$_6$)alkyl and linear or branched (C$_1$-C$_6$)alkyl-carbonyl, β) or to reducing conditions in the presence of NaBH$_4$ to yield the compounds of formula (I/k), a particular case of the compounds of formula (I):

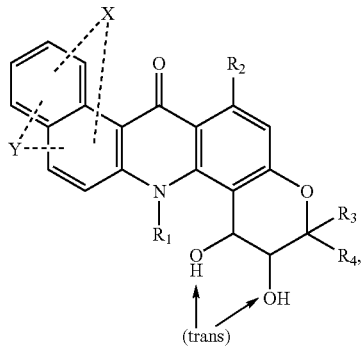
(I/k)

wherein X, Y, R$_1$, R$_2$, R$_3$ and R$_4$ are as defined hereinbefore, the totality of the compounds of formulae (cis-I/g) and (I/k) constituting the compounds of formula (I/l),

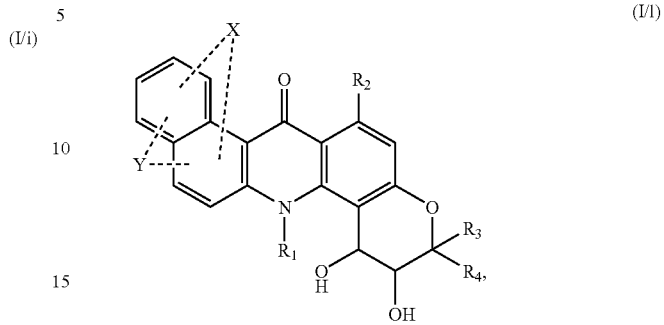
(I/l)

wherein X, Y, R$_1$, R$_2$, R$_3$ and R$_4$ are as defined hereinbefore,

γ) or to the action of a tosylate chloride, followed by the action of NaN$_3$ in the presence of hydrogen peroxide, followed by a reduction step, to yield the compounds of formula (I/m), a particular case of formula (I):

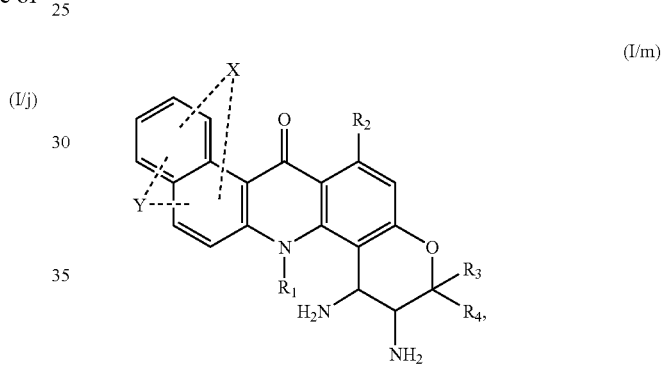
(I/m)

wherein X, Y, R$_1$, R$_2$, R$_3$ and R$_4$ are as defined hereinbefore,

Which Compounds of Formula (I/n) are Subjected 1) either to the action of carbon dioxide, in the presence of diphenyl phosphite, to yield the compounds of formula (I/n), a particular case of the compounds of formula (I):

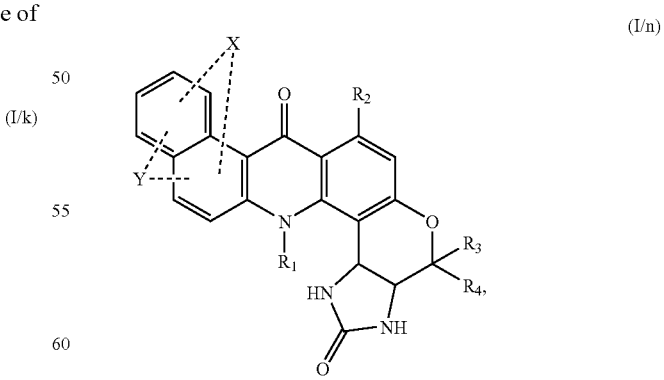
(I/n)

wherein X, Y, R$_1$, R$_2$, R$_3$ and R$_4$ are as defined hereinbefore, 2) or to the action of a compound of formula (XII):

Hal-G'$_1$    (XII), wherein Hal is as defined hereinbefore and G'₁ represents a group selected from —R_c, C(W₂)—U—V, C(W₂)—W₃-T₁, S(O)_n—W₃-T₁ and S(O)_n—U'—V', wherein R_c, W₂, W₃, U, V, U',
V', T₁ and n are as defined for formula (I), to yield the compounds of formulae (I/O₁), (I/O₂) and (I/O₃), particular cases of the compounds of formula (I):

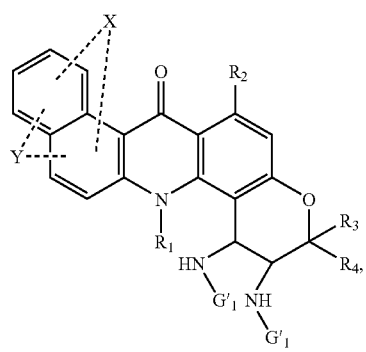

(I/o₁)

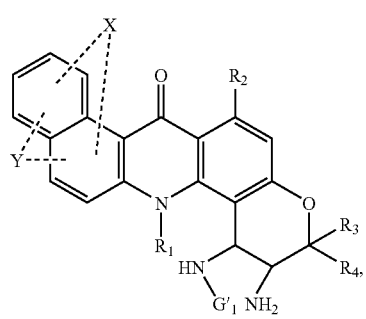

(I/o₂)

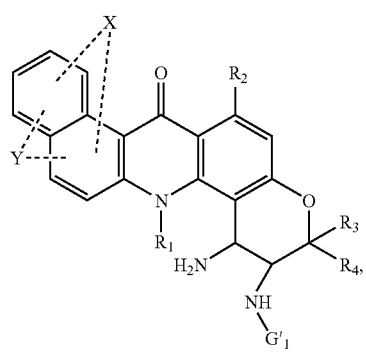

(I/o₃)

wherein X, Y, R₁, R₂, R₃, R₄ and G'₁ are as defined hereinbefore,
the primary amine function of which compounds of formulae (I/O₂) and (I/O₃) is protected by a protecting group for primary amine groups to yield the compounds of formulae (XIII/a) and (XIII/b),

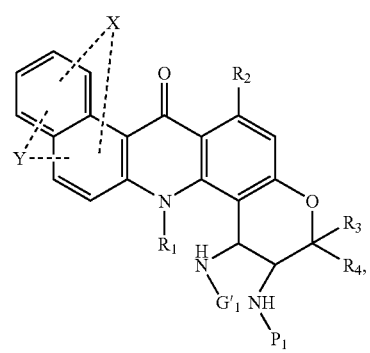

(XIII/a)

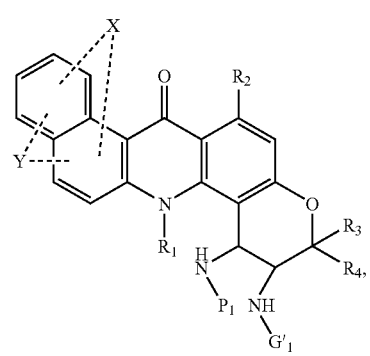

(XIII/b)

wherein X, Y, R₁, R₂, R₃, R₄ and G'₁ are as defined hereinbefore and P₁ represents a protecting group for primary amine groups,
which compounds of formulae (I/O₁), (XIII/a) and (XIII/b) are, if desired subjected to the action of a compound of formula (XIV):

R_{c1}-Hal     (XIV), wherein Hal represents a halogen and R_{c1} represents a group selected from linear or branched (C₁-C₆)alkyl, aryl and aryl-(C₁-C₆)alkyl wherein the alkyl moiety is linear or branched, and then, in the case of compounds of formulae (XIII/a) and (XIII/b), are subjected to conditions deprotecting the primary amine function to yield the compounds of formulae (I/p₁), (I/p₂) and (I/p₃), particular cases of the compounds of formula (I):

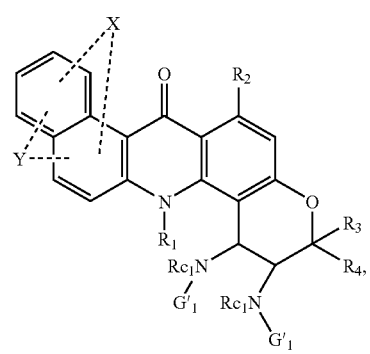

(I/p₁)

-continued (I/p2)

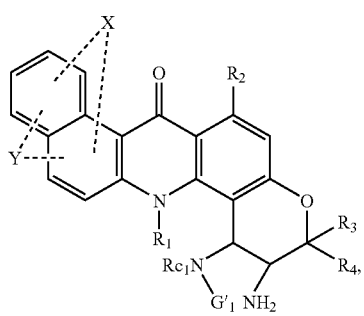

(I/p3)

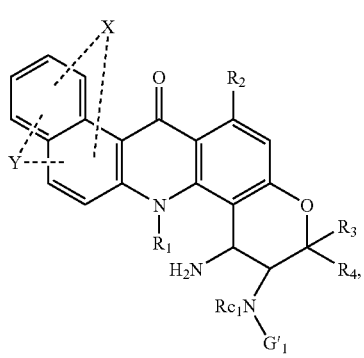

wherein X, Y, $R_1$, $R_2$, $R_3$, $R_4$, $G'_1$ and $R_{c1}$ are as defined hereinbefore, which compounds of formulae (I/p2) and (I/p3) are, if desired subjected successively to the action of a compound of formula (XIV) as defined hereinbefore and then of a compound of formula (XV):

$R_{d'1}$-Hal     (XV)

wherein Hal is as defined hereinbefore and $R_{d'1}$ may take the same definitions as $R_{c1}$, to yield the compounds of formulae (I/q2) and (I/q3), particular cases of the compounds of formula (I):

(I/q2)

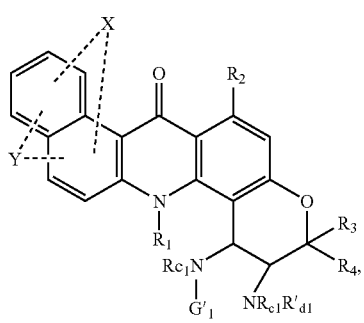

(I/q3)

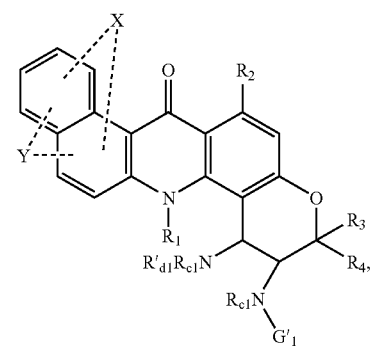

wherein X, Y, $R_1$, $R_2$, $R_3$, $R_4$, $G'_1$, $R_1$ and $R_d$, are as defined hereinbefore, It being Possible for the Compounds of Formula (I/l) to be Subjected α) to the action of a compound of formula (XII) as defined hereinbefore to yield the compounds of formulae (I/$r_1$), (I/$r_2$) and (I/$r_3$), particular cases of the compounds of formula (I):

(I/$r_1$)

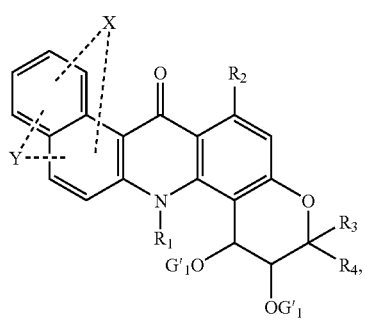

(I/$r_2$)

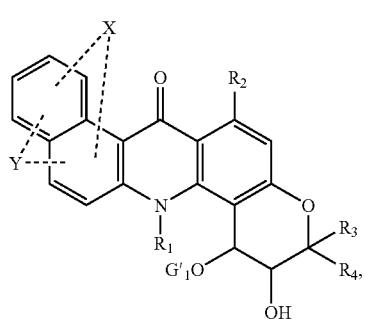

(I/$r_3$)

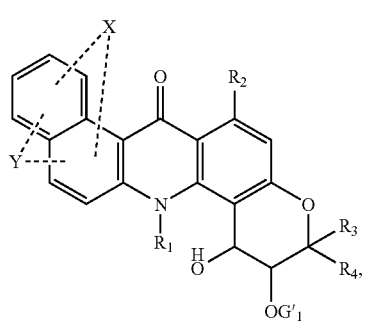

wherein X, Y, $R_1$, $R_2$, $R_3$, $R_4$ and $G'_1$ are as defined hereinbefore, Which Compounds of Formula (I/$r_1$) are Subjected:
1) either, when $G'_1$ represents a group $C(W_2)$—U—V, to the action of an alcohol of formula $R_{30}$—OH, wherein $R_{30}$ represents a linear or branched ($C_1$-$C_6$)alkyl group, to yield the compounds of formula (I/$s_1$), a particular case of the compounds of formula (I):

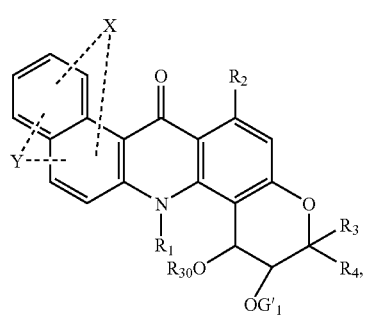
(I/$s_1$)

wherein X, Y, $R_1$, $R_2$, $R_3$, $R_4$, $G'_1$ and $R_{30}$ are as defined hereinbefore, 2) or, when $G'_1$ represents a group $C(W_2)$—U—V, to the action of a thiol of formula (XVI):

$G_1S$—H     (XVI), wherein $G_1$ represents a group selected from $R_c$, $C(W_2)$—U—V and $C(W_2)$—$W_3$-$T_1$, wherein $R_c$, $W_2$, $W_3$, U, V and $T_1$ are as defined for formula (I), to yield the compounds of formula (I/$t_1$), a particular case of the compounds of formula (I):

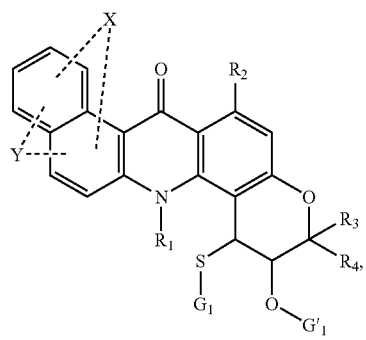
(I/$t_1$)

wherein X, Y. $R_1$, $R_2$, $R_3$, $R_4$, $G_1$ and $G'_1$ are as defined hereinbefore, which compounds of formula (I/$t_1$) are, if desired treated with a reducing agent and are then subjected to a reaction deprotecting the hydroxy function to yield the compounds of formula (I/$u_1$), a particular case of the compounds of formula (I):

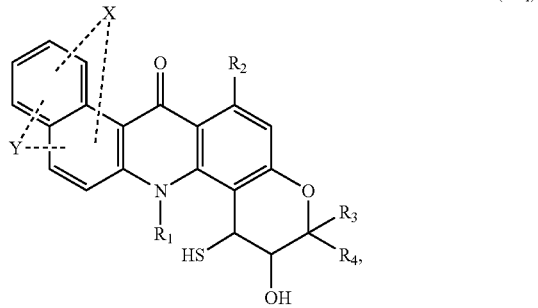
(I/$u_1$)

wherein X, Y, $R_1$, $R_2$, $R_3$ and $R_4$ are as defined hereinbefore,

Which Compounds of Formulae (I/$r_2$) and (I/$r_3$) are Subjected:
1) either to the action of an anhydride of formula (XVII) or of an acid chloride of formula (XVIII):

[V—U—$C(W_2)$]$_2$O     (XVII),

Cl—$C(W_2)$—U—V     (XVIII), wherein $W_2$, U and V are as defined for formula (I), to yield the compounds of formulae (I/$v_2$) and (I/$V_3$), particular cases of the compounds of formula (I):

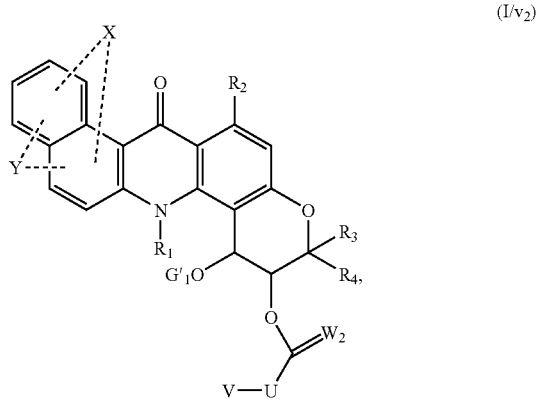
(I/$v_2$)

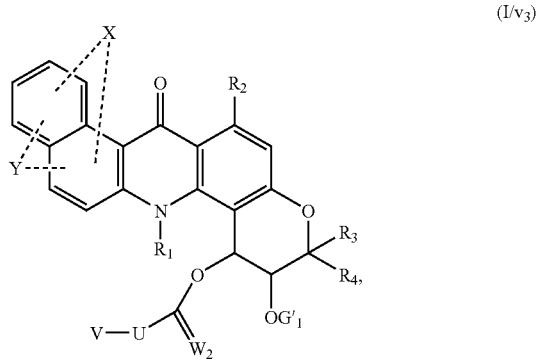
(I/$v_3$)

wherein X, Y, $R_1$, $R_2$, $R_3$, $R_4$, $G'_1$, $W_2$, U and V are as defined hereinbefore,
2) or to dehydrating conditions in an acid medium to yield the compounds of formulae (I/$W_2$) and (I/$W_3$), particular cases of the compounds of formulae (I):

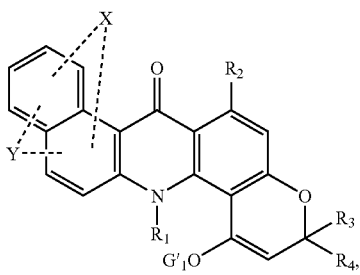
(I/w₂)

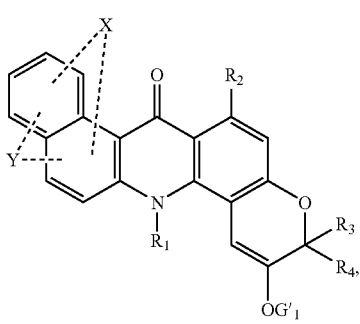
(I/w₃)

wherein X, Y, R₁, R₂, R₃, R₄ and G'1 are as defined hereinbefore,

β) or to the action of a compound of formula (XIX) or (XX)

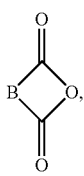
(XIX)

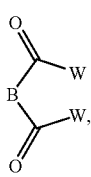
(XX)

wherein B is as defined for formula (I) and W represents a halogen atom or a hydroxyl group, to yield the compounds of formula (I/x), a particular case of the compounds of formula (I):

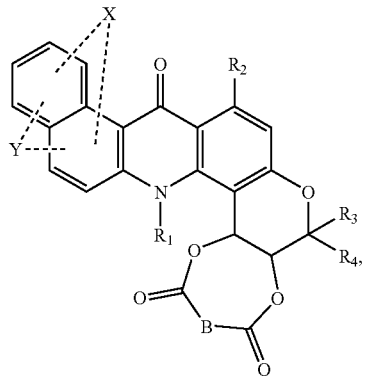
(I/x)

wherein X, Y, R₁, R₂, R₃, R₄ and B are as defined hereinbefore,

γ) or to the action of a linear ($C_1$-$C_6$)alkyl dihalide to yield the compounds of formula (I/y), a particular case of the compounds of formula (I):

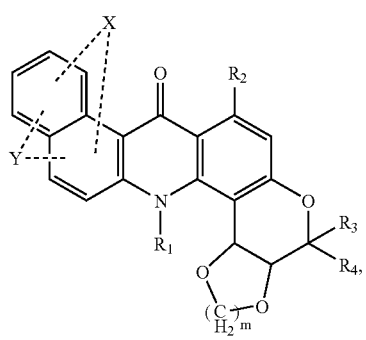
(I/y)

wherein X, Y, R₁, R₂, R₃ and R₄ are as defined hereinbefore and m is as defined for formula (I), δ) or to the action of one equivalent of a compound of formula (XVII) or (XVIII) to yield the compounds of formula (I/z), a particular case of the compounds of formula (I):

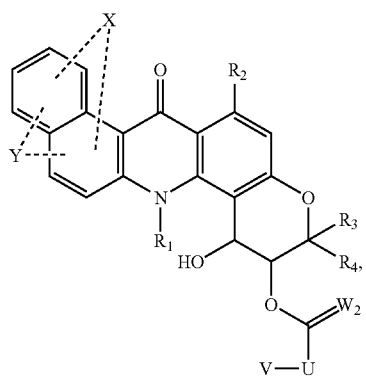
(I/z)

wherein X, Y, R₁, R₂, R₃, R₄, W₂, U and V are as defined hereinbefore, which compounds of formula (I/z) may be subjected to an excess of anhydride of formula (XVII') or of an acid chloride of formula (XVIII')

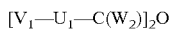 (XVII'),

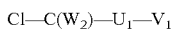 (XVIII'), wherein U₁ and V₁ may take the same definitions as U and V, and W₂ is as defined hereinbefore, to yield the compounds of formula (I/aa), a particular case of the compounds of formula (I):

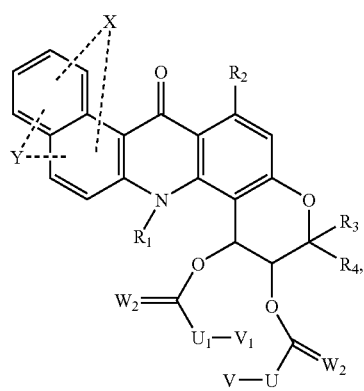

(I/aa)

wherein X, Y, R₁, R₂, R₃, R₄, W₂, U, V, U₁ and V₁ are as defined hereinbefore,

ε) or to dehydrating conditions in an acid medium to yield the compounds of formula (I/ab), a particular case of the compounds of formula (I):

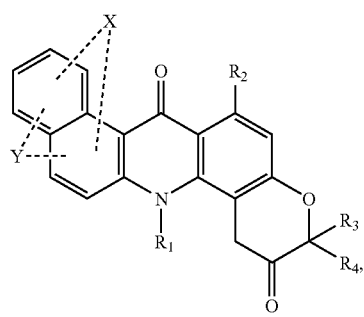

(I/ab)

wherein X, Y, R₁, R₂, R₃ and R₄ are as defined hereinbefore, which compounds of formula (I/ab) are, if desired reduced in the presence of NaBH₄ to yield the compounds of formula (I/ac), a particular case of the compounds of formula (I):

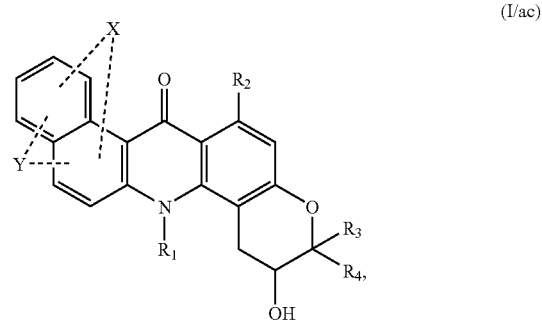

(I/ac)

wherein X, Y, R₁, R₂, R₃ and R₄ are as defined hereinbefore, d) or to the action of a peracid or of dimethyl dioxirane to yield the compounds of formula (I/ad), a particular case of the compounds of formula (I):

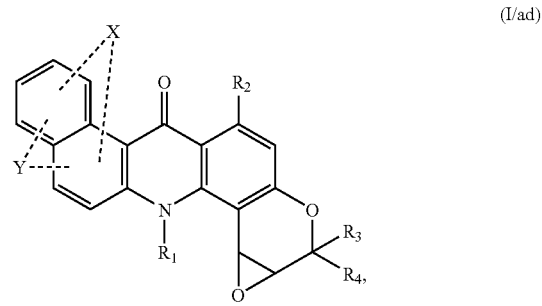

(I/ad)

wherein X, Y, R₁, R₂, R₃ and R₄ are as defined hereinbefore, which compounds of formula (I/ad) are, if desired treated with ammonia or with a primary or secondary amine to yield the compounds of formulae (I/ae₁) and (I/ae₂), particular cases of the compounds of formula (I):

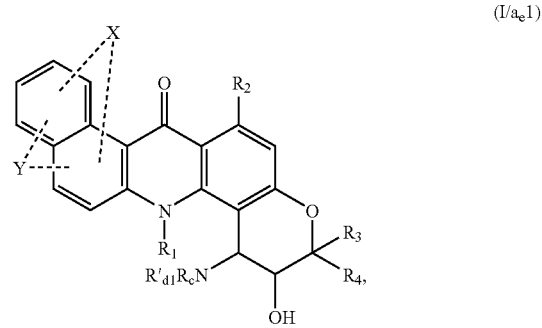

(I/ae1)

-continued (I/ae2)

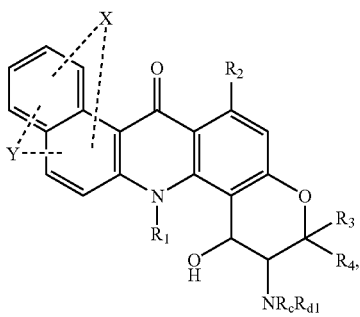

wherein X, Y, $R_1$, $R_2$, $R_3$ and $R_4$ are as defined hereinbefore, $R_c$ is as defined for formula (I) and $R_{d1}$ represents a group selected from $R_d$, —C($W_2$)—U—V, —C($W_2$)—$W_3$-$T_1$, —S(O)$_n$—$W_3$-$T_1$ and —S(O)$_n$—U'—V', wherein $R_d$, $W_2$, $W_3$, U, V, $T_1$, U' and V' are as defined hereinbefore, It Being Possible for the Compounds of Formulae (I/ae$_1$) and (I/ae$_2$) to be Subjected α), when $R_c$ and $R_{d1}$ each represent a hydrogen atom, to the action of a compound of formula (XI) as defined hereinbefore to yield the compounds of formulae (I/af$_1$) and (I/af$_2$), particular cases of the compounds of formula (I):

(I/af1)

(I/af2)

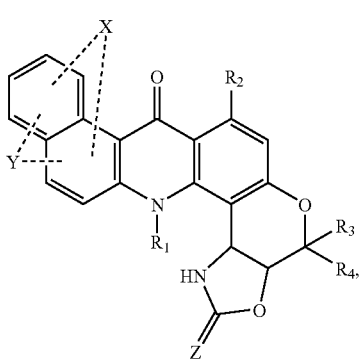

wherein X, Y, $R_1$, $R_2$, $R_3$, $R_4$ and Z are as defined hereinbefore,

β) or to the action of a compound of formulae (XIX) or (XX) as defined hereinbefore to yield the compounds of formulae (I/ag$_1$) and (I/ag$_2$), particular cases of the compounds of formula (I):

(I/ag1)

(I/ag2)

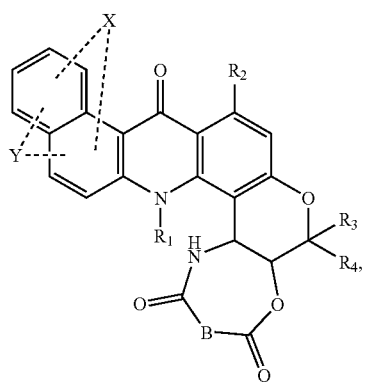

wherein X, Y, $R_1$, $R_2$, $R_3$, $R_4$ and B are as defined hereinbefore,

γ) or to the action of a compound of formula (XII) as defined hereinbefore to yield the compounds of formulae (I/ah$_1$) and (I/ah$_2$), particular cases of the compounds of formula (I):

(I/ah1)

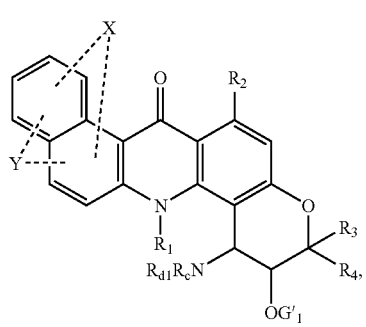

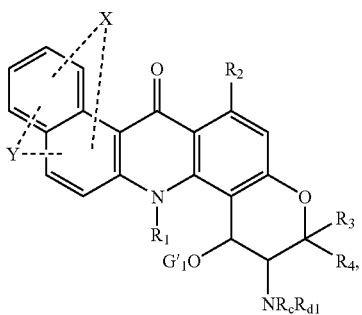

(I/a_h2)

wherein X, Y, $R_1$, $R_2$, $R_3$, $R_4$, $R_c$, $R_{d1}$ and $G'_1$ are as defined hereinbefore, δ) or to the action of triphenylphosphine dibromide in the presence of triethylamine to yield the compounds of formulae (I/ai), a particular case of the compounds of formula (I):

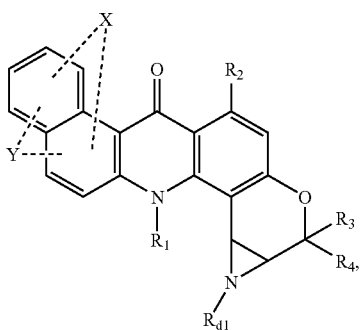

(I/ai)

wherein X, Y, $R_1$, $R_2$, $R_3$, $R_4$ and $R_{d1}$ are as defined hereinbefore, ε) or to dehydrating conditions in an acid medium to yield the compounds of formulae (I/aj$_2$) and (I/aj$_3$), particular cases of the compounds of formula (I):

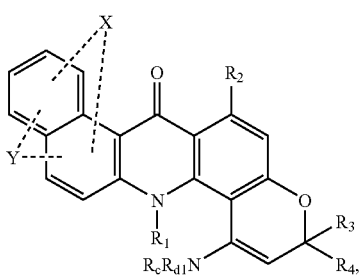

(I/aj2)

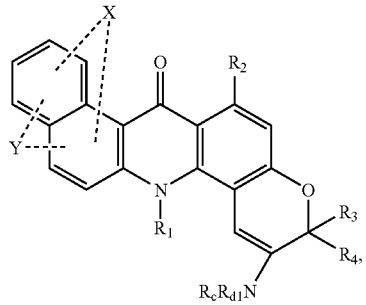

(I/aj3)

wherein X, Y, $R_1$, $R_2$, $R_3$, $R_4$, $R_c$ and $R_{d1}$ are as defined hereinbefore, e) or to the action of a compound of formula (XXI):

$$\text{Hal-C(W}_2\text{)-T}_1 \quad \quad \text{(XXI)},$$

wherein Hal represents a halogen atom, and $W_2$ and $T_1$ are as defined for formula (I), to yield the compounds of formula (I/aj), a particular case of the compounds of formula (I):

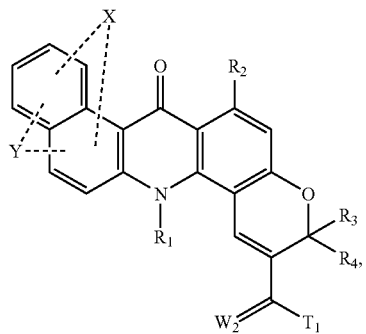

(I/aj)

wherein X, Y, $R_1$, $R_2$, $R_3$, $R_4$, $W_2$ and $T_1$ are as defined hereinbefore, the compounds (I/a) to (I/aj) constituting the totality of the compounds of the invention, which are purified, if necessary, according to a conventional purification technique, which may be, if desired, separated into their different isomers according to a conventional separation technique and which are converted, if desired, into their N-oxides and, where appropriate, their addition salts with a pharmaceutically acceptable acid or base.

The compounds of formulae (II), (IV), (IX) to (XII), (XIV) to (XXI), (XVIII') and (XVIII') either are commercially available compounds or are obtained according to conventional methods of organic synthesis well known to the person skilled in the art.

The compounds of formula (I) wherein A represents a group of formula —CH($R_5$)—CH($R_6$), wherein $R_5$ and $R_6$, which may be the same or different, represent, each independently of the other, a group selected from a hydrogen atom, an $OR_c$ group and a $W_1$—C($W_2$)—U—V group, wherein $R_c$ is as defined for formula (I), $W_1$ and $W_2$ each represent an oxygen atom, U represents a linear or branched ($C_1$-$C_8$)alkylene chain and V represents a hydrogen atom, or R and $R_6$ together form a group

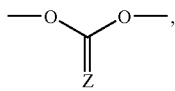

wherein Z is as defined for formula (I), may be advantageously obtained starting from compounds of formula (I/e):

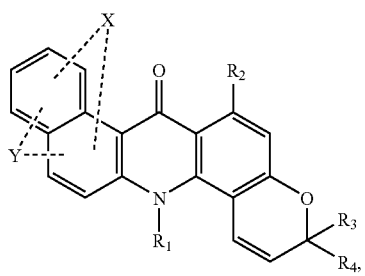

(I/e)

wherein X, Y, $R_1$, $R_2$, $R_3$ and $R_4$ are as defined hereinbefore, which are subjected to the action of osmium tetroxide in a polar medium and in the presence of 4-methylmorpholine N-oxide, or to the action of potassium permanganate followed by reduction using sodium borohydride to yield, depending on the method, the cis- or trans-diol compounds of formula (I/ak), a particular case of the compounds of formula (I):

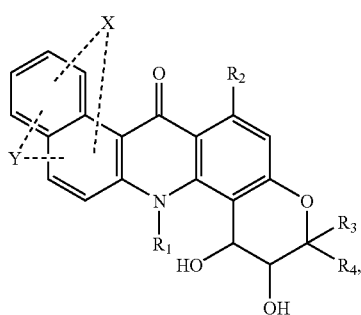

(I/ak)

wherein X, Y, $R_1$, $R_2$, $R_3$ and $R_4$ are as defined hereinbefore, which cis-diol compounds of formula (cis-I/ak) are, if desired, subjected either to the action of N,N'-carbonyldiimidazole or of N,N'-thiocarbonyldiimidazole in the presence of 2-butanone to yield the compounds of formula (cis-I/al), a particular case of the compounds of formula (I):

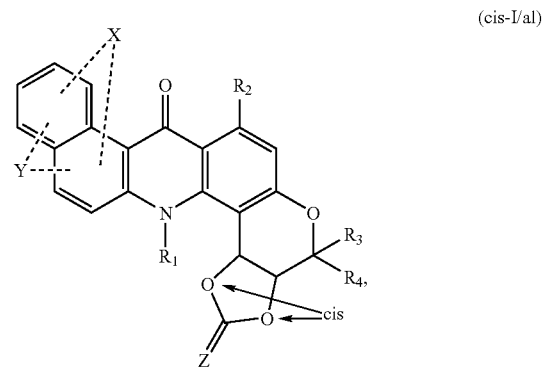

(cis-I/al)

wherein X, Y, $R_1$, $R_2$, $R_3$ and $R_4$ are as defined hereinbefore and Z is as defined for formula (I), or to the action of a compound of formula (XXII) or of a compound of formula (XXIII):

Hal-$G_2$ (XXII), or $G_2$-O-$G_2$ (XXIII), wherein Hal represents a halogen atom and $G_2$ represents a group selected from —C($W_2$)—U—V, —C($W_2$)—$W_3$-$T_1$, —S(O)$_n$—$W_3$-$T_1$ and —S(O)$_n$—U'—V', wherein $W_2$, $W_3$, U, V, U', V' and n are as defined for formula (I), to yield the compounds of formula (I/am), a particular case of the compounds of formula (I):

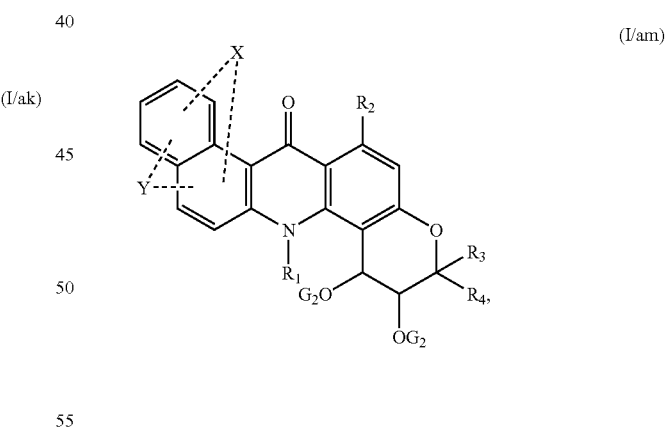

(I/am)

wherein X, Y, $R_1$, $R_2$, $R_3$, $R_4$ and $G_2$ are as defined hereinbefore, the compound of formula (I/am) constituting the totality of the compounds of the invention, which are purified, if necessary, according to a conventional purification technique, which may be, if desired, separated into their different isomers according to a conventional separation technique and which are converted, if desired, into their N-oxides and, where appropriate, their addition salts with a pharmaceutically acceptable acid or base.

The compounds of formulae (XXII) and (XXIII) either are commercially available compounds or are obtained according to conventional methods of organic synthesis well known to the person skilled in the art.

The compounds of formula (I) have especially valuable anti-tumour properties. They have excellent in vitro cytotoxicity with respect to cell lines originating from murine and human tumours, by virtue of specific blockage of the cell cycle, and are active in vivo, in the mouse, with respect to transplantable murine and human tumours. The characteristic properties of these compounds allow them to be used therapeutically as anti-tumour agents.

The present invention relates also to pharmaceutical compositions comprising, as active ingredient, at least one compound of formula (I), an enantiomer or diastereoisomer thereof, or an N-oxide thereof, or an addition salt thereof with a pharmaceutically acceptable acid or base, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, intravaginal, rectal, nasal, perlingual; buccal, ocular or respiratory administration.

Pharmaceutical compositions according to the invention for parenteral injections especially include aqueous and non-aqueous sterile solutions, dispersions, suspensions or emulsions and also sterile powders for reconstituting injectable solutions or dispersions.

Pharmaceutical compositions according to the invention for solid oral administrations especially include tablets or dragées, sublingual tablets, sachets, gelatin capsules and granules, and for liquid oral, nasal, buccal or ocular administrations especially include emulsions, solutions, suspensions, drops, syrups and aerosols.

Pharmaceutical compositions for rectal or vaginal administration are preferably suppositories and those for per- or trans-cutaneous administration especially include powders, aerosols, creams, ointments, gels and patches.

The pharmaceutical compositions mentioned hereinbefore illustrate the invention but do not limit it in any way.

Among the inert, non-toxic, pharmaceutically acceptable excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colourants, aromatising agents etc.

The useful dosage varies according to the age and weight of the patient, the administration route, the pharmaceutical composition used, the nature and severity of the disorder and the administration of any associated treatments. The dosage ranges from 0.1 mg to 1000 mg per day in one or more administrations.

The Examples that follow illustrate the invention but do not limit it in any way.

The starting materials used are products that are known or that are prepared according to known operating procedures. The various Preparations yield synthesis intermediates that are useful in preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given refers to the salt form of the compound.

PREPARATION 1:
N-(3,5dimethoxyphenyl)acetamide

A solution of 15.3 g of 3,5-dimethoxyaniline and 57.5 ml of acetic anhydride in 40 ml of anhydrous pyridine is heated at reflux for 1 hour. The reaction mixture is then cooled and poured into 350 ml of water. The precipitate formed is suspended in 20% aqueous $Na_2CO_3$ solution and is then filtered off using a Buchner funnel, washed with water and dried under a phosphoric vacuum. A precipitate of 14.5 g of the expected product is obtained in the form of a white amorphous solid.

Mass spectrum ($DIC/NH_3$): m/z=196 $(M+H)^+$

PREPARATION 2:
9,11-Dihydroxybenzo[a]acridin-12(7H)-one

Step A: Methyl 2-methoxy-1-naphthoate 54 ml of dimethyl sulphate are added to a solution of 26.32 g of 2-hydroxy-1-naphthoic acid in 70 ml of 4.5N aqueous NaOH solution. The reaction mixture is then maintained at ambient temperature, with stirring, for 4 hours, diluted with 250 ml of water and extracted with dichloromethane (4×100 ml). The combined organic phases are washed with water, dried over sodium sulphate and evaporated to dryness under reduced pressure. Chromatography over silica gel (cyclohexane and then a gradient of from 1 to 10% acetone in the cyclohexane) allows 21.5 g of the expected product to be isolated.

Mass spectrum ($DIC/NH_3$): m/z=217 $(M+H)^+$

Step B: 2-Methoxy-1-naphthoic acid

A solution of 21.6 g of the compound of Step A above in 48 ml of Claisen's alkali solution (solution of 21 g of KOH in 15 ml of water, made up to 60 ml with methanol) is heated at reflux for 4 hours. The reaction mixture is then diluted with 50 ml of water and poured into 75 ml of 15.5% hydrochloric acid solution cooled to 0° C. with stirring. The white precipitate formed is then filtered off over a Buchner funnel and then washed with water and dried under a phosphoric vacuum. The dry residue obtained is dissolved in a solution of ethanol and water (80:20, v/v) at boiling. After cooling to 0° C., 13.7 g of the expected product are obtained.

Melting Point: 56-57° C. Mass Spectrum ($DIC/NH_3$): m/z=203 $(M+H)^+$

Step C: N-[3,5-dimethoxy-2-(2-methoxy-1-naphthoyl)phenyl]acetamide 30 ml of $SOCl_2$ are added dropwise, over 30 minutes, to 15.15 g of the compound of Step B above in a flask fitted with a condenser and connected to a gas trap. The reaction mixture is then heated at 60° C. for 3 hours and evaporated to dryness under reduced pressure. The 2-methoxy-1-naphthoic acid chloride thereby obtained is dissolved in 50 ml of anhydrous dichloroethane and added dropwise to a mixture of 12.5 g of $AlCl_3$ and 12.7 g of the compound of Preparation 1 in 100 ml of anhydrous dichloroethane previously cooled to 0° C. The reaction mixture is maintained at 0° C. for 3 hours and then at 20° C. for 3 hours. The reaction mixture is then poured into 250 ml of 15% hydrochloric acid solution previously cooled in an ice bath with stirring and is extracted with dichloromethane (3×40 ml). The combined organic phases are washed with $NaHCO_3$ solution and then with water, dried over anhydrous sodium sulphate, filtered and evaporated to dryness under reduced pressure. Chromatography over silica gel (dichloromethane and then a gradient of from 0.2 to 4% methanol in the dichloromethane) allows 7.74 g of the expected product to be isolated.

Melting Point: 149-150° C. Mass Spectrum (DIC/NH$_3$): m/z=379 (M+H)$^+$

Step D: 9,11-Dimethoxybenzo[a]acridin-12(7H)-one

A solution of 3.79 g of the compound of Step C above in 60 ml of anhydrous dimethylformamide is added dropwise to a suspension of 1.2 g of NaH in 50 ml of anhydrous dimethylformamide previously cooled to 0° C. The reaction mixture is maintained at 0° C. with stirring and under an inert atmosphere for 15 minutes and is then maintained at 20° C. for 4 hours 30 minutes. The reaction mixture is then poured into 200 ml of water and extracted with ethyl acetate (3×50 ml). The combined organic phases are washed successively with NaOH solution and then with water, dried over anhydrous sodium sulphate, filtered and then evaporated to dryness under reduced pressure. Chromatography over silica gel (dichloromethane and then a gradient of from 0.5 to 5% of methanol in the dichloromethane) allows 2.05 g of the expected product to be obtained.

Melting Point: 258-259° C. Mass Spectrum (DIC/NH$_3$): m/z=305 (M+H)$^+$

Step E: 9,11-Dihydroxybenzo[α]acridin-12(7H)-one 80 ml of 48% aqueous HBr solution are added to a solution of 1.89 g of the compound of Step D above in 90 ml of acetic acid and is then heated at reflux for 4 days. After cooling, the reaction mixture is poured into 1000 ml of ice-cold water. The brown precipitate formed is filtered off over a Buchner funnel, washed with water and dried under a phosphoric vacuum. Chromatography over silica gel (dichloromethane and then a gradient of from 1% to 10% methanol in the dichloromethane) allows 1.55 mg of the expected product to be obtained.

Melting Point: 311-312° C. Mass Spectrum (DIC/NH$_3$): m/z=278 (M+H)$^+$

PREPARATION 3: N-(3-methoxyphenyl)acetamide

The compound is obtained according to the procedure of Preparation 1, using 3-methoxyaniline instead of the 3,5-dimethoxyaniline.

PREPARATION 4:
9-Hydroxybenzo[a]acridin-12(7H)-one

Step A: N-[5-methoxy-2-(2-methoxy-1-naphthoyl)phenyl]acetamide

The compound is obtained according to the procedure of Step C of Preparation 2, using the compound of Preparation 3 instead of the compound of Preparation 1.

Step B: 9-Methoxybenzo[a]acridin-12(7H)-one

The compound is obtained according to the procedure of Step D of Preparation 2, using the compound of Step A above.

Step C: 9-Hydroxybenzo[α]acridin-12(7H)-one

The compound is obtained according to the procedure of Step E of Preparation 2, using the compound of Step B above.

PREPARATION 5:
3-Bromo-9,11-dihydroxybenzo[a]acridin-12(711)-one

The compound is obtained according to the procedure of Preparation 2, Step A through Step E, using 6-bromo-2-hydroxy-1-naphthoic acid instead of 2-hydroxy-1-naphthoic acid.

Mass Spectrum (ESI$^+$): m/z=354 (M+H)$^+$

EXAMPLE 1

6-Hydroxy-3,3-dimethyl-3,14-dihydro-7H-benzo[a]
pyrano[3,2-h]-acridin-7-one 732 mg of the compound of Preparation 2 are dissolved in 20 ml of anhydrous dimethylformamide and then 732 mg of anhydrous potassium carbonate are added. The mixture thereby obtained is stirred under argon, at 65° C., for 15 minutes and then 876.5 mg of anhydrous potassium iodide and 2.47 g of 3-chloro-3-methyl-1-butyne are added. At the end of 5 hours, the reaction mixture is heated at 130° C. for 2 hours in order to bring about the rearrangement of the propargyl ether. The reaction mixture is then diluted with 50 ml of water and extracted with dichloromethane (3×40 ml). The combined organic phases are washed with water and then with 1M potassium hydroxide solution, dried over anhydrous sodium sulphate, filtered and then evaporated to dryness under reduced pressure. Chromatography over silica gel (cyclohexane and then a gradient of from 1 to 5% acetone in the cyclohexane) allows 326 mg of the expected product to be obtained.

Mass spectrum (DIC/NH$_3$): m/z=345 (M+H)$^+$

EXAMPLE 2

6-Hydroxy-3,3,14-trimethyl-3,14-dihydro-7H-benzo
[a]pyrano[3,2-h]-acridin-7-one 1.324 g of sodium carbonate are added to 411.6 mg of the compound of Example 1 dissolved in 50 ml of anhydrous acetone. The mixture is maintained, with stirring, under argon and at 0° C. for 15 minutes and then, after adding 852 mg of methyl iodide, the reaction mixture is heated at reflux for 2 hours. After cooling, the excess of methyl iodide is destroyed by the addition of 40 ml of methanol and 50 ml of water. The methanol is removed by distillation and the aqueous phase is extracted with dichloromethane (3×30 ml). The combined organic phases are washed with 10% aqueous NaOH solution and then with water, dried over anhydrous sodium sulphate and then filtered and evaporated to dryness under reduced pressure. Chromatography carried out over silica gel (cyclohexane and then a gradient of from 0.5 to 5% acetone in the cyclohexane) allows 374.2 mg of the expected product to be obtained.

Mass Spectrum (DIC/NH$_3$): nm/z=358 (M+H)$^+$

EXAMPLE 3

6-Methoxy-3,3,14-trimethyl-3,14-dihydro-7H-benzo
[a]pyrano[3,2-h]-acridin-7-one

A solution of 604.3 mg of the compound of Example 2 in 40 ml of anhydrous acetone is gradually added to a suspension, maintained under argon and at 0° C., of 61 mg of sodium hydride in 10 ml of acetone. The mixture thereby obtained is maintained at 0° C. for 30 minutes and then 1.2 g of methyl iodide are added. The reaction mixture is heated at reflux for 6 hours. After cooling, the excess of methyl iodide is destroyed by the addition of 40 ml of methanol and 50 ml of water. The methanol is removed by distillation and the aqueous phase is extracted with dichloromethane (3×30 ml). The combined organic phases are washed with 10% aqueous NaOH solution and then with water, dried over anhydrous sodium sulphate and then filtered and evaporated to dryness under reduced pressure. Chromatography over silica gel (cyclohexane and then a gradient of from 1 to 10% acetone in the cyclohexane) allows 469.5 mg of the expected product to be isolated.

Mass spectrum (DIC/NH$_3$): m/z=372 (M+H)$^+$

EXAMPLE 4

(±)-Cis-1,2-Dihydroxy-6-methoxy-3,3,14-trimethyl-1,2,3,14-tetrahydro-7H-benzo[a]pyrano[3,2-h]acridin-7-one A mixture of 0.4859 g of the compound of Example 3, osmium tetroxide (2.5%) dissolved in 1.05 ml of 2-methyl-2-propanol and 96.7 mg of 4-methylmorpholine N-oxide monohydrate is dissolved in 40 ml of a mixture of tert-BuOH:THF:H$_2$O (10:3:1). The reaction mixture is maintained, with stirring, at ambient temperature for 4 days. Saturated NaHSO$_3$ solution (30 ml) is then added. After stirring for one hour, the reaction mixture is extracted with dichloromethane (4×25 ml). The combined organic phases are dried over anhydrous sodium sulphate and then filtered and evaporated to dryness under reduced pressure. Chromatography over silica gel (cyclohexane and then a gradient of from 1 to 15% acetone in the cyclohexane) allows 452.7 mg of the expected product to be isolated.

Mass Spectrum (DIC/NH$_3$): m/z=406 (M+H)$^+$

EXAMPLE 5

(±)-cis-1,2-Diacetoxy-6-methoxy-3,3,14-trimethyl-1,2,3,14-tetrahydro-7H-benzo[α]pyrano[3,2-h]-acridin-7-one 61 mg of the compound of Example 4 and 1 mg of DMAP are added to a mixture, previously cooled (in an ice bath), of anhydrous pyridine (4 ml) and acetic anhydride (0.4 ml). The reaction mixture is maintained, with stirring, at ambient temperature for 3 days, protected from light. The reaction mixture is then poured into 10 ml of ice-cold H$_2$O, the precipitate formed is filtered off, washed with H$_2$O (2×5 ml) and then dried under a phosphoric vacuum. 62.4 mg of the expected product crystallises from a mixture of dichloromethane:ethyl acetate (9:1, v/v) in the form of fine white prisms.

Melting Point: 161-162° C. Mass Spectrum (DIC/NH$_3$): m/z=477 (M+H)$^+$

EXAMPLE 6

(±)-cis-7-Methoxy-4,4,15-trimethyl-15,15c-dihydro-4H-benzo[α][1,3]-dioxolo[4',5':4,5]pyrano[3,2-h]acridine-2,8[3aH]-dione 230.5 mg of N,N'-carbonyldiimidazole are added to a solution of 109.4 mg of the compound of Example 4 in 5 ml of 2-butanone. The reaction mixture is maintained at reflux for 3 hours and is then, after cooling, diluted with 5% aqueous Na$_2$CO$_3$ solution (7 ml) and extracted with ethyl acetate (3×10 ml). The combined organic phases are dried over anhydrous sodium sulphate and then filtered and evaporated to dryness under reduced pressure. Chromatography over silica gel (dichloromethane and then a gradient of from 1 to 7% acetone in the dichloromethane) allows 65.7 mg of the expected product to be obtained.

Mass Spectrum (DIC/NH$_3$): m/z=432 (M+H)$^+$

EXAMPLE 7

(±)-cis-1-{[(Dimethylamino)carbonyl]oxy}-6-methoxy-3,3,14-trimethyl-7-oxo-2,3,7,14-tetrahydro-1H-benzo[α]pyrano[3,2-h]-acridin-2-yl dimethylcarbamate At −10° C., add a solution of 0.123 mmol of the compound of Example 4 in 4 ml of anhydrous tetrahydrofuran to 0.698 mmol of potassium hydride washed with hexane. After the dropwise addition, at −10° C., of 0.327 mmol of N,N-dimethylcarbamoyl chloride, stirring is carried out for 3 hours 30 minutes at ambient temperature. After adding 50 ml of ethyl acetate and 10 ml of saturated NaHCO$_3$ solution, the organic phase is washed with water, dried over magnesium sulphate and then evaporated under reduced pressure to yield the expected product.

EXAMPLE 8

(±)-cis-6-Methoxy-3,3,14-trimethyl-2-{[(4-methylphenyl)sulphonyl]-oxy}-7-oxo-2,3,7,14-tetrahydro-1H-benzo[α]pyrano[3,2-h]acridin-1-yl 4-methylbenzenesulphonate The compound is obtained according to the procedure of Example 7, using tosyl chloride instead of the N,N-dimethylcarbamoyl chloride.

EXAMPLE 9

(±)-cis-{[1-(Acetyloxy)-6-methoxy-3,3,14-trimethyl-7-oxo-2,3,7,14-tetrahydro-1H-benzo[α]pyrano[3,2-h]acridin-2-yl]oxy}-4-oxobutanoic acid To a solution of 0.5 mmol of the compound of Example 4 in 3 ml of anhydrous pyridine there are added 1.1 equivalents of succinic anhydride and 1 mg of dimethylaminopyridine. Stir for 2 days in the dark and at ambient temperature, then add 25 ml of acetic anhydride at −15° C. and stir for 1.5 hours before concentrating under reduced pressure. Chromatography over silica gel (dichloromethane/acetic acid: 99/1) allows the expected product to be isolated.

EXAMPLE 10

(±)-cis-5-{[(1-(Acetyloxy)-6-methoxy-3,3,14-trimethyl-7-oxo-2,3,7,14-tetrahydro-1H-benzo[α]pyrano[3,2-h]acridin-2-yl]oxy}-5-oxopentanoic acid The compound is obtained according to the procedure of Example 9, using glutaric anhydride instead of the succinic anhydride.

EXAMPLE 11

(±)-cis-1-(Acetyloxy)-6-methoxy-3,3,14-trimethyl-7-oxo-2,3,7,14-tetrahydro-1H-benzo[α]pyrano[3,2-h]acridin-2-yl [(tert-butoxycarbonyl)amino]acetate Slowly add 0.6 mmol of dicyclohexylcarbodiimide to a solution, at 0° C., of 0.5 mmol of the compound of Example 4 and 0.5 mmol of 2-[(tert-butoxycarbonyl)amino]acetic acid in 10 ml of dimethylformamide. The reaction mixture is maintained at 0° C. for 5 hours and then at ambient temperature for 16 hours. After filtration and evaporation under reduced pressure, the residue is dissolved in 2 ml of anhydrous pyridine; 2 ml of acetic anhydride are added, and the mixture is stirred for 48 hours at ambient temperature and in the dark. After concentrating the reaction mixture under reduced pressure, chromatography of the residue over silica gel (dichloromethane) allows the expected product to be isolated.

EXAMPLE 12

(±)-cis-1-(Acetyloxy)-6-methoxy-3,3,14-trimethyl-7-oxo-2,3,7,14-tetrahydro-1H-benzo[α]pyrano[3,2-h]acridin-2-yl aminoacetate Add 0.14 µl of iodotrimethylsilane to a solution, at ambient temperature, of 0.1 mmol of the compound of Example 11 in 1 ml of chloroform. The reaction mixture is stirred at ambient temperature for 5 minutes and then evaporated to dryness under reduced pressure. Chromatography over silica gel (dichloromethane/methanol:85/15) allows the expected product to be isolated.

EXAMPLE 13

2-Butyryl-6-methoxy-3,3,14-trimethyl-3,14-dihydro-7H-benzo[α]-pyrano[3,2-h]acridin-7-one A mixture of 0.81 mmol of butyryl chloride and 0.673 mmol of AlCl$_3$ in 2 ml of anhydrous dichloromethane is added, in small portions, to 0.135 mmol of the product of Example 3 in 2 ml of dichloromethane at 0° C. The reaction mixture is stirred for 4 hours at ambient temperature and then poured into a 10% HCl solution. After conventional treatment of the organic phases and evaporation thereof under reduced pressure, chromatography of the residue over silica gel (dichloromethane/methanol) allows the expected product to be isolated.

EXAMPLE 14

(±)-cis-1-Hydroxy-6-methoxy-3,3,14-trimethyl-7-oxo-2,3,7,14-tetrahydro-1H-benzo[α]pyrano[3,2-h]acridin-2-yl butyrate Add 2 equivalents of butyryl chloride to a solution of 0.74 mmol of the compound of Example 4 in the presence of 4-dimethylaminopyridine in 7 ml of anhydrous pyridine. Stir at ambient temperature for 72 hours and then add 5 equivalents of butyryl chloride and resume stirring for 72 hours; then evaporate to dryness. Chromatography over silica gel allows the expected product to be isolated.

EXAMPLE 15

6-Methoxy-3,3,14-trimethyl-7-oxo-7,14-dihydro-3H-benzo[α]pyrano-[3,2-h]alacridin-2-yl butyrate Add 4 drops of 10% HCl solution to a solution of 0.29 mmol of the compound of Example 14 in 6 ml of dichloromethane. The reaction mixture is stirred for 3 days at ambient temperature and is then dried and concentrated under reduced pressure. Chromatography of the residue over silica gel (dichloromethane/methanol) allows the expected product to be isolated.

EXAMPLE 16

2-Hydroxy-6-methoxy-3,3,14-trimethyl-2,3-dihydro-1H-benzo[α]-pyrano[3,2-h]acridine-1,7(14h)-dione Over a period of 30 minutes, add a suspension of 1.28 g of KMnO$_4$ in 15 ml of water dropwise to a solution of 0.5 g of the product of Example 3 dissolved in 25 ml of acetone. The reaction mixture is stirred at ambient temperature for 8 hours and then, after extraction and conventional treatment, the expected product is isolated by chromatography of the residue over silica gel (dichloromethane/methanol: 98/2).

EXAMPLE 17

6-Methoxy-3,3,14-trimethyl-1,7-dioxo-2,3,7,14-tetrahydro-1H-benzo[α]pyrano[3,2-h]acridin-2-yl acetate The compound is obtained according to the procedure of Example 14, starting from the compound of Example 16, using acetic anhydride instead of the butyryl chloride.

EXAMPLE 18

3,3-Dimethyl-3,14-dihydro-7H-benzo[α]pyrano[3,2-h]acridin-7-one

The compound is obtained according to the procedure of Example 1, using the compound of Preparation 4 instead of the compound of Preparation 2.

EXAMPLE 19

3,3,14-Trimethyl-3,14-dihydro-7H-benzo[α]pyrano[3,2-h]acridin-7-one

The compound is obtained according to the procedure of Example 2, using the compound of Example 18 instead of the compound of Example 2.

EXAMPLE 20

(±)-cis-1,2-Dihydroxy-3,3,14-trimethyl-1,2,3,14-tetrahydro-7H-benzo[α]pyrano[3,2-h]acridin-7-one The compound is obtained according to the procedure of Example 4, using the compound of Example 19 instead of the compound of Example 3.

EXAMPLE 21

(±)-cis-1-(Acetyloxy)-3,3,14-trimethyl-7-oxo-2,3,7, 14-tetrahydro-1H-benzo[α]pyrano[3,2-h]acridin-2-yl acetate The compound is obtained according to the procedure of Example 5, using the compound of Example 20 instead of the compound of Example 4.

EXAMPLE 22

1-Hydroxy-6-methoxy-3,3,14-trimethyl-7-oxo-2,3,7, 14-tetrahydro-1H-benzo[α]pyrano[3,2-h]acridin-2-yl acetate 2.2 mmol of acetic anhydride are added to a solution, cooled to 0° C., of 2 mmol of the compound of Example 4 in 5 ml of anhydrous pyridine. After stirring at ambient temperature for 3 hours, the reaction mixture is concentrated under reduced pressure. Chromatography over silica gel (dichloromethane, and then dichloromethane/methanol: 99/1) allows the expected product to be isolated.

EXAMPLE 23

1-(Acetyloxy)-6-methoxy-3,3,14-trimethyl-7-oxo-2, 3,7,14-tetrahydro-1H-benzo[α]pyrano[3,2-h]acridin-2-yl benzoate The compound is obtained according to the procedure of Example 9, using benzoic anhydride instead of the succinic anhydride.

EXAMPLE 24

1-1Hydroxy-6-methoxy-3,3,14-trimethyl-7-oxo-2,3, 7,14-tetrahydro-1H-benzo[α]pyrano[3,2-h]acridin-2-yl propionate The compound is obtained according to the procedure of Example 22, using propionic anhydride instead of the acetic anhydride.

EXAMPLE 25

6-Methoxy-3,3,14-trimethyl-7-oxo-1-(propionyloxy)-2,3,7,14-tetrahydro-1H-benzo[α]pyrano[3,2-h] acridin-2-yl propionate The compound is obtained according to the procedure of Example 5, using propionic anhydride instead of the acetic anhydride.

EXAMPLE 26

1-Hydroxy-6-methoxy-3,3,14-trimethyl-7-oxo-2,3,7, 14-tetrahydro-1H-benzo[α]pyrano[3,2-h]acridin-2-yl 4-pentenoate The compound is obtained according to the procedure of Example 14, using pentenoic anhydride instead of the butyryl chloride.

EXAMPLE 27

6-Methoxy-3,3,14-trimethyl-7-oxo-1-(4-pentenoyloxy)-2,3,7,14-tetrahydro-1H-benzo[α]pyrano[3,2-h] acridin-2-yl 4-pentenoate The compound is obtained according to the procedure of Example 14, using pentenoic anhydride instead of the butyryl chloride. Chromatography over silica gel (dichloromethane, and then dichloromethane/methanol: 99/1 to 98/2) allows the expected product to be isolated.

EXAMPLE 28

1-(Acetyloxy)-6-methoxy-3,3,14-trimethyl-7-oxo-2, 3,7,14-tetrahydro-1H-benzo[α]pyrano[3,2-h]acridin-2-yl 4-pentenoate The compound is obtained according to the procedure of Example 9, using pentenoic anhydride instead of the succinic anhydride.

EXAMPLE 29

6-Methoxy-3,3,14-trimethyl-1-[(3-methylbutanoyl) oxy]-7-oxo-2,3,7,14-tetrahydro-1H-benzo[α]pyrano [3,2-h]acridin-2-yl 3-methylbutanoate The compound is obtained according to the procedure of Example 5, using isovaleryl chloride instead of the acetic anhydride.

EXAMPLE 30

4-{[1-(Acetyloxy)-6-methoxy-3,3,14-trimethyl-7-oxo-2,3,7,14-tetrahydro-1H-benzo[α]pyrano[3,2-h] acridin-2-yl]oxy}-4-oxobutanoic acid The compound is obtained according to the procedure of Example 9 using an excess of succinic anhydride. Chromatography over silica gel (dichloromethane, and then dichloromethane/methanol: 99/1) allows the expected product to be obtained.

EXAMPLE 31

5-({-[(4-Carboxybutanoyl)oxy]-6-methoxy-3,3,14-trimethyl-7-oxo-2,3,7,14-tetrahydro-1H-benzo[α] pyrano[3,2-h]acridin-2-yl}oxy)-5-oxopentanoic acid The compound is obtained according to the procedure of Example 9, using glutaric anhydride in excess instead of the succinic anhydride.

EXAMPLE 32

1-{[(Diethylamino)carbonyl]oxy}-6-methoxy-3,3, 14-trimethyl-7-oxo-2,3,7,14-tetrahydro-1H-benzo[α] pyrano[3,2-h]acridin-2-yl diethylcarbamate The compound is obtained according to the procedure of Example 7, using N,N-diethylcarbamoyl chloride instead of the N,N-dimethylcarbamoyl chloride.

EXAMPLE 33

6-{[2-(Dimethylamino)ethyl)amino}-3,3,14-trimethyl-3,14-dihydro[α]pyrano[3,2-h]acridin-7-one 4 ml of N,N-dimethylethylenediamine are added to 0.15 g of the product of Example 3. After reacting for 5 days at 70° C. under an inert atmosphere, the reaction mixture is evaporated under reduced pressure. The residue obtained is chromatographed over silica gel (cyclohexane/ethyl acetate: 80/20), allowing the expected product to be obtained.
Melting point: oil.

EXAMPLE 34

6-{[3-(Diethylamino)propyl)amino}-3,3,14-trimethyl-3,14-dihydro[α]pyrano[3,2-h]acridin-7-one The procedure is as in Example 33, using N,N-diethylpropyldiamine as reagent.
Melting point: oil.

EXAMPLE 35

1-Hydroxy-6-methoxy-3,3,14-trimethyl-7-oxo-2,3,7,14-tetrahydro-1H-benzo[α]pyrano[3,2-h]acridin-2-yl (2E)-3-phenyl-2-propenoate 1.33 mmol of cinnamoyl chloride are added to a previously cooled solution of 0.30 mmol of the compound of Example 4 in 4 ml of pyridine. After stirring at 0° C. for 90 minutes, the reaction mixture is evaporated under reduced pressure. Chromatography over silica gel (cyclohexane, and then cyclohexane/acetone: 94/6 to 90/10) allows the expected product to be isolated.

EXAMPLE 36

1-(Acetyloxy)-6-methoxy-3,3,14-trimethyl-7-oxo-2,3,7,14-tetrahydro-1H-benzo[α]pyrano[3,2-h]acridin-2-yl(2E)-3-phenyl-2-propenoate 31 mmol of acetic anhydride are added to a previously cooled solution of 0.18 mmol of the compound of Example 35 in 3 ml of pyridine. After stirring at ambient temperature for 3 days, the reaction mixture is evaporated under reduced pressure. Chromatography over silica gel (cyclohexane/acetone: 94/6) allows the expected product to be isolated.

EXAMPLE 37

6-Methoxy-3,3-dimethyl-3,14-dihydro-7H-benzo[α]pyrano[3,2-h]acridin-7-one

A solution of 300 mg of compound of Example 1 in 15 ml of anhydrous dimethylformamide is added dropwise to a suspension of 125 mg of sodium hydride in 10 ml of anhydrous dimethylformamide previously cooled to 0° C. The reaction mixture is maintained at 0° C. for 15 minutes, at room temperature for 30 minutes and then 0.57 ml of dimethylsulfate are added. After 17 hours, the reaction mixture is poured into 150 ml of ice-cold water and extracted with dichloromethane (3×50 ml). The combined organic phases are dried over anhydrous sodium sulphate and then filtered and evaporated to dryness under reduced pressure. Chromatography over silica gel (cyclohexane and then a gradient of acetone 5 to 20%) allowing the expected product to be obtained.
Mass spectrum (ESI): m/z=358 (M+H)$^+$

EXAMPLE 38

(±)-cis-1-Hydroxy-6-methoxy-3,3,14-trimethyl-3,14-dihydro-7H-benzo[α]pyrano[3,2-h]acridin-2-yl dimethylcarbamate At −10° C., add a solution of 0.124 mmol of the compound of Example 4 in 8 ml of anhydrous tetrahydrofuran to 1.24 mmol of potassium hydride washed with hexane. After the dropwise addition, at −10° C., of 0.49 mmol of N,N-dimethylcarbamoyl chloride, stirring is carried out for 3 hours 20 hours at ambient temperature. After adding 25 ml of ethyl acetate and 10 ml of saturated NaHCO$_3$ solution, the organic phase is washed with water, dried over sodium sulphate and then evaporated under reduced pressure. Chromatography over silica gel (dichloromethane/acetone: 80/20) allows the expected product to be obtained.
Mass spectrum (ESI): m/z=477 (M+H)$^+$

EXAMPLE 39

10-Bromo-6-hydroxy-3,3-dimethyl-3,14-dihydro-7H-benzo[α]-pyrano[3,2-h]-acridin-7-one The compound is obtained according to the procedure of Example 1, using the compound of Preparation 5 instead of the compound of Preparation 2.
Mass spectrum (ESI$^+$): m/z=422 (M+H)$^+$

EXAMPLE 40

10-Bromo-6-methoxy-3,3,14-trimethyl-3,14-dihydro-7H-benzo[α]-pyrano[3,2-h]-acridin-7-one The compound is obtained according to the procedure of Example 3, using the compound of Example 39 instead of the compound of Example 2.
Mass spectrum (ESI$^+$): m/z=450 (M+H)$^+$

EXAMPLE 41

10-Bromo-6-hydroxy-3,3,14-trimethyl-3,14-dihydro-7H-benzo[α]-pyrano[3,2-h]acridin-7-one The compound is obtained according to the procedure of Example 2, using the compound of Example 39 instead of the compound of Example 1.

Pharmacological Study of Compounds of the Invention

EXAMPLE 42

In Vitro Cytotoxicity

Four cell lines were used:
1 murine leukaemia: L1210,
1 human epidermoid carcinoma: KB-3-1,
1 human colon carcinoma: HT29,
1 human prostate carcinoma: LNCap.

The cells are cultured in RPMI 1640 complete culture medium containing 10% foetal calf serum, 2 mM glutamine, 50 units/ml of penicillin, 50 μg/ml of streptomycin and 10 mM Hepes, pH=7.4. The cells are distributed on microplates and are exposed to the cytotoxic compounds. The cells are then incubated for 2 days (L1210) or 4 days (human lines). The number of viable cells is then quantified by a colorimetric assay, the Microculture Tetrazolium Assay (Cancer Res. 1987, 47, 939-942). The results are expressed in terms of the $IC_{50}$ (the concentration of cytotoxic agent which inhibits proliferation of the treated cells by 50%). By way of example, the compounds of Examples 5 and 6 have an $IC_{50}$ of 0.73 µM and 0.06 µM, respectively, with respect to L1210 and of 0.14 µM and 0.015 µM, respectively, with respect to KB-3-1. The compound of Example 5 has an $IC_{50}$ of 1.18 µM with respect to HT-29 and of 0.57 µM with respect to LNCap.

EXAMPLE 43

In Vivo Activity

Anti-Tumour Activity with Respect to C38 Adenocarcinoma of the Colon

Tumour fragments of C38 adenocarcinoma of the colon weighing approximately 30 mg were implanted under the skin of B6D2F1 mice (Iffa Credo, France) on day 0. After growth of the tumour, the mice were divided into control (18 animals) and treated (6 or 7 animals) groups, which were homogeneous with respect to tumour size. The products were administered twice by the i.v. route on days 12 and 22, at their Maximum Tolerated Dose (MTD), MTD/2 and MTD/4.

The tumours were measured twice a week and the tumour volumes were calculated according to the following formula: volume (mm³)=length (mm)×breadth (mm²)/2.

The anti-tumour activity is expressed as % T/C:

$$\% \ T/C = \frac{\text{median } Vt/V0 \text{ of the treated animals}}{\text{median } Vt/V0 \text{ of the control animals}} \times 100$$

V0 and Vt being the initial volume of the tumour and its volume at measurement time t, respectively.

The optimum dose is the dose giving the lowest T/C value without toxicity (early death or weight loss greater than 20%).

By way of example, the compound of Example 5 exhibit an inhibition of the tumour growth of 95% (T/C=5%) at the optimum dose of 4 mg/kg, whereas acronycine exhibits a T/C of 27% at the optimum dose of 100 mg/kg, thereby demonstrating their strong therapeutic potential.

EXAMPLE 44

Pharmaceutical Composition: Injectable Solution

| Compound of Example 6 | 10 mg |
| Distilled water for injectable preparations | 25 ml |

What is claimed is:

1. A compound selected from those of formula (I):

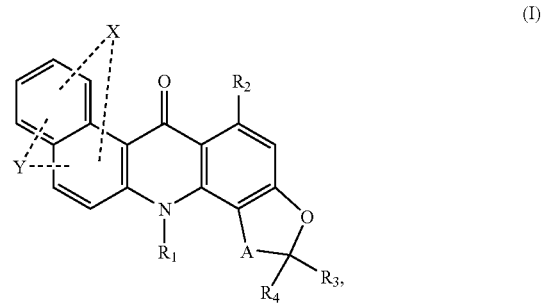

wherein:
X and Y, which may be the same or different, represent, independently of one another, a group selected from: hydrogen, halogen, hydroxy, linear or branched ($C_1$-$C_6$) alkoxy, nitro, cyano, linear or branched ($C_1$-$C_6$)alkyl, linear or branched ($C_2$-$C_6$)alkenyl and linear or branched ($C_1$-$C_6$)polyhaloalkyl, and —$NR_aR_b$, wherein:

$R_a$ and $R_b$, which may be the same or different, represent, independently of one another, a group selected from hydrogen, —C(O)—$CF_3$, —C(O)—$NH_2$ and linear or branched ($C_1$-$C_6$)alkyl optionally substituted by $NR'_aR'_b$, wherein:

$R'_a$ and $R'_b$, which may be the same or different, represent, independently of one another, a group selected from hydrogen, linear or branched ($C_1$-$C_6$)alkyl, aryl and aryl-($C_1$-$C_6$)alkyl in which the alkyl moiety is linear or branched, or $R'_a$ and $R'_b$, together with the nitrogen atom carrying them, form a monocyclic, 5- to 7-membered heterocycle optionally containing in the cyclic system a second hetero atom selected from oxygen and nitrogen, or $R_a$ and $R_b$, together with the nitrogen atom carrying them, form a monocyclic, 5- to 7-membered heterocycle optionally containing in the cyclic system a second hetero atom selected from oxygen and nitrogen, it being understood that the substituents X and Y may be present on either of the two adjacent benzene rings, $R_1$ represents hydrogen or linear or branched ($C_1$-$C_6$) alkyl, $R_2$ represents a group selected from hydrogen, linear or branched ($C_1$-$C_6$)alkyl, —$OR''_a$, —$NR'_aR'_b$, —O-$T_a$-$OR''_a$, —$NR''_a$-$T_a$-$NR'_aR'_b$, —$NR''_a$—C(O)-$T_a$H, —O—C(O)-$T_a$H, —O-$T_a$-$NR'_aR'_b$, —$NR''_a$-$T_a$-$OR''_a$, —$NR''_a$-$T_a$-$CO_2R''_a$ and —$NR''_a$—C(O)-$T_a$-$NR'_aR'_b$, wherein:

$T_a$ represents linear or branched ($C_1$-$C_6$)alkylene, $R'_a$ and $R'_b$ are as defined hereinbefore, $R''_a$ represents a group selected from hydrogen and linear or branched ($C_1$-$C_6$)alkyl, $R_3$ and $R_4$, which may be the same or different, represent, independently of one another, hydrogen or linear or branched ($C_1$-$C_6$)alkyl, or $R_3$ and $R_4$, together with the carbon atom carrying them, form a monocyclic, 3- to 6-membered cyclic group, A represents a group of formula:

—CH($R_5$)—CH($R_6$)—, wherein:

$R_5$ and $R_6$, which may be the same or different, represent, independently of one another, a group selected from:
hydrogen,
$OR_c$, $NR_cNR_d$ and $SR_c$, wherein:
  $R_c$ and $R_d$, which may be the same or different, represent, independently of one another, a group selected from hydrogen, linear or branched ($C_1$-$C_6$)alkyl, aryl, aryl-($C_1$-$C_6$)alkyl in which the alkyl moiety is linear or branched, and C(O)—$R_e$, wherein $R_e$ represents a group selected from hydrogen, aryl and $NR'''_aR'''_b$, wherein $R'''_a$ and $R'''_b$, which may be the same or different, represent, independently of one another hydrogen or linear or branched ($C_1$-$C_6$)alkyl, or
  $R'''_a$ and $R'''_b$, together with the nitrogen atom carrying them, form a monocyclic, 5- to 7-membered heterocycle optionally containing in the cyclic system a second hetero atom selected from oxygen and nitrogen,
$W_1$—C($W_2$)—U—V, wherein:
  $W_1$ represents oxygen, sulphur or $NR_c$ wherein $R_c$ is as defined hereinbefore,
  $W_2$ represents oxygen or sulphur,
  U represents linear or branched ($C_1$-$C_8$)alkylene or linear or branched ($C_2$-$C_8$)alkenylene,
  V represents a group selected from:
    hydrogen,
    aryl,
    —$OR_c$, $CO_2R_c$, $COR_c$, $CONR'_aR'_b$, $NR'_aR'_b$, $N(R_c)$—$CO_2R'_c$ and $N(R_c)$—$COR'_c$, wherein $R'_a$, $R'_b$ and $R_c$ are as defined hereinbefore and $R'_c$ represents a group selected from hydrogen, linear or branched ($C_1$-$C_6$)alkyl, aryl and aryl-($C_1$-$C_6$)alkyl in which the alkyl moiety is linear or branched,
  it being understood that U represents a bond when $W_2$ does not represent an oxygen atom and when simultaneously V does not represent a group selected from hydrogen, aryl and $NH_2$,
$W_1$—C($W_2$)—$W_3$-$T_1$, wherein:
  $W_1$ and $W_2$ are as defined hereinbefore,
  $W_3$ represents oxygen, sulphur or $NR_c$, wherein $R_c$ is as defined hereinbefore,
  $T_1$ represents a group selected from:
    hydrogen,
    linear or branched ($C_1$-$C_6$)alkyl,
    linear or branched ($C_2$-$C_6$)alkenyl,
    aryl, aryl-($C_1$-$C_6$)alkyl in which the alkyl moiety is linear or branched,
    linear or branched ($C_1$-$C_6$)alkylene and linear or branched ($C_2$-$C_6$)alkenylene, each being substituted by a group selected from $OR_c$ and $NR'_aR'_b$, wherein $R_c$, $R'_a$ and $R'_b$ are as defined hereinbefore,
$W_1$—S(O)$_n$—$W_3$-$T_1$, wherein:
  $W_1$, $W_3$ and $T_1$ are as defined hereinbefore, n represents an integer selected from 1 and 2,
$W_1$—S(O)$_n$—U'—V', wherein:
  U' represents linear or branched ($C_1$-$C_8$)alkylene or linear or branched ($C_2$-$C_8$)alkenylene,
  V' represents a group selected from:
    hydrogen,
    aryl,
    $OR_c$, $CO_2R_c$, $COR_c$, $CONR'_aR'_b$, $NR'_aR'_b$, $N(R_c)$—$CO_2R'_c$ and $N(R_c)$—$COR'_c$ wherein $R'_a$, $R'_b$, $R_c$ and $R'_c$ are as defined hereinbefore,
  $W_1$ and n are as defined hereinbefore,
C($W_2$)-$T_1$, wherein $W_2$ and $T_1$ are as defined hereinbefore,
or $R_5$ and $R_6$ together form:

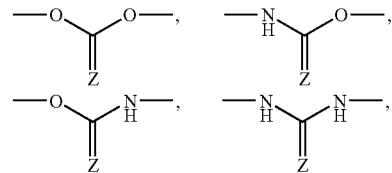

wherein Z represents oxygen or sulphur,
—O—($CH_2$)$_m$—O—, wherein m represents an integer of from 1 to 4 inclusive,

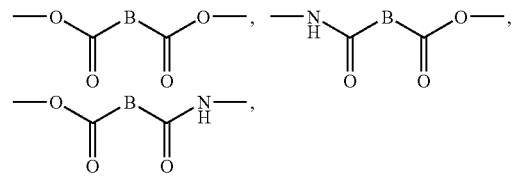

wherein B represents single bond, linear or branched ($C_1$-$C_6$)alkylene or linear or branched ($C_2$-$C_6$)alkenylene,
or $R_5$ and $R_6$, together with the carbon atoms carrying them, form oxirane or aziridine optionally substituted on the nitrogen atom by linear or branched ($C_1$-$C_6$) alkyl, —CH=C($R_7$)— or —C($R_7$)=CH—, wherein $R_7$ represents a group selected from:
hydrogen,
$OR''_a$, $W_1$—C($W_2$)—U—V, $W_1$—C($W_2$)—$W_3$-$T_1$, $W_1$—S(O)$_n$—$W_3$-$T_1$, $W_1$—S(O)$_n$—U'—V' and C($W_2$)-$T_1$, wherein $R''_a$, $W_1$, $W_2$, $W_3$, U, V, U', V', $T_1$, and n are as defined hereinbefore, —C(O)—CH($R_8$)— or —CH($R_8$)—C(O)—, wherein $R_8$ represents a group selected from:
hydrogen,
linear or branched ($C_1$-$C_6$)alkyl-carbonyloxy and $OR''_a$, wherein $R''_a$ is as defined hereinbefore,
its enantiomers, diastereoisomers, N-oxides, and addition salts thereof with a pharmaceutically acceptable acid or base,
it being understood that:
"aryl" may be "phenyl" or "naphthyl", each of those groups being optionally substituted by one or more, identical or different, substituents selected from hydroxy, halogen, carboxy, nitro, amino, linear or branched ($C_1$-$C_6$)alkylamino, di($C_1$-$C_6$)alkylamino wherein each alkyl moiety may be linear or branched, linear or branched ($C_1$-$C_6$)alkoxy, linear or branched ($C_1$-$C_6$)acyl or linear or branched ($C_1$-$C_6$)alkyl-carbonyloxy, and optical isomers thereof.

2. A compound of claim 1 which is a compound of formula (IA):

(IA)

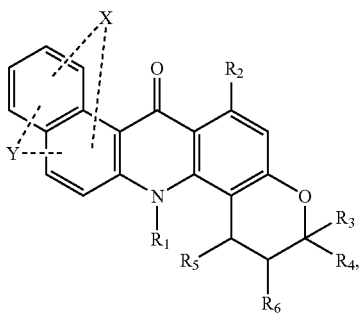

3. A compound of claim 2, wherein $R_5$ and $R_6$, which may be the same or different, each represent a group of formula —$OR_c$, $W_1$—$C(W_2)$—U—V, $W_1$—$C(W_2)$—$W_3$-$T_1$, $C(W_2)$-$T_1$, or $R_5$ and $R_6$ together form

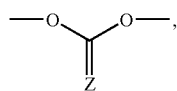

wherein $R_c$, $W_1$, $W_2$, $W_3$, U, V, $T_1$ and Z are as defined for formula (I).

4. A compound of claim 2, wherein $R_5$ and $R_6$ are identical and each represent a group of formula —$OR_c$, wherein $R_c$ represents hydrogen.

5. A compound of claim 2, wherein $R_5$ and $R_6$ are identical or different and each represent a group of formula $W_1$—C$(W_2)$—U—V, wherein $W_1$ and $W_2$ each represent oxygen, U is as defined for formula (I) and V represents hydrogen or U represents linear or branched $(C_1$-$C_8)$alkylene and V represents $NR'_aR'_b$, wherein $R'_a$ and $R'_b$, which may be the same or different, each represent hydrogen or linear or branched $(C_1$-$C_6)$alkyl.

6. A compound of claim 2, wherein $R_5$ represents a group of formula —$OR_c$, wherein $R_c$ represents hydrogen, and $R_6$ represents a group of formula $W_1$—$C(W_2)$—U—V, wherein $W_1$ and $W_2$ each represent oxygen, U represents linear or branched $(C_1$-$C_8)$alkylene and V represents hydrogen.

7. A compound of claim 2, wherein $R_5$ represents a group of formula —$OR_c$, or $W_1$—$C(W_2)$—U—V, wherein $R_c$ represents hydrogen, $W_1$ and $W_2$ each represent oxygen, U represents linear or branched $(C_1$-$C_8)$alkylene and V represents hydrogen, and $R_6$ represents a group of formula $W_1$—$C(W_2)$—U—V, wherein $W_1$ and $W_2$ each represent oxygen, U represents linear or branched $(C_2$-$C_8)$alkenylene and V represents hydrogen or aryl.

8. A compound of claim 2, wherein $R_5$ and $R_6$, which may be the same or different, each represent a group of formula $W_1$—$C(W_2)$—$W_3$-$T_1$, wherein $W_1$ and $W_2$ each represent oxygen, $W_3$ represents —$NR_c$, wherein $R_c$ represents linear or branched $(C_1$-$C_6)$alkyl, and $T_1$ represents linear or branched $(C_1$-$C_6)$alkyl.

9. A compound of claim 2, wherein $R_5$ and $R_6$ together form

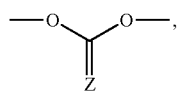

wherein Z represents oxygen.

10. A compound of claim 1, which is a compound of formula (IB):

(IB)

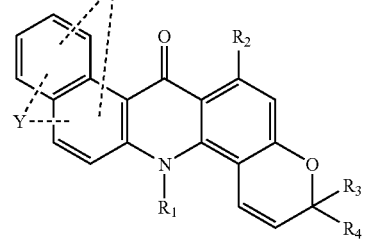

11. A compound of claim 1, wherein $R_3$ and $R_4$ each represent linear or branched $(C_1$-$C_4)$alkyl.

12. A compound of claim 1, wherein $R_3$ and $R_4$ each represent methyl.

13. A compound of claim 1, wherein $R_2$ represents —$OR''_a$ or —$NR''_a$-$T_a$-$NR'_aR'_b$, wherein $R'_a$, $R'_b$, $R''_a$ and $T_a$ are as defined for formula (I).

14. A compound of claim 1, wherein $R_2$ represents —$OR''_a$ or —$NR''_a$-$T_a$-$NR'_aR'_b$, wherein $R''_a$ and $T_a$ are as defined for formula (I), and $R'_a$ and $R'_b$, which may be the same or different, each represent linear or branched $(C_1$-$C_6)$ alkyl.

15. A compound of claim 1, wherein X and Y each represent hydrogen.

16. A compound of claim 1 which is selected from:
- (±)-cis-1,2-dihydroxy-6-methoxy-3,3,14-trimethyl-1,2,3,14-tetrahydro-7H-benzo[α]pyrano[3,2-h]acridin-7-one,
- (±)-cis-1,2-diacetoxy-6-methoxy-3,3,14-trimethyl-1,2,3,14-tetrahydro-7H-benzo[α]pyrano[3,2-h]acridin-7-one,
- (±)-cis-7-methoxy-4,4,15-trimethyl-15,15c-dihydro-4H-benzo[α][1,3]dioxolo-[4',5':4,5]pyrano[3,2-h]acridine-2,8(3aH)-dione,
- 6-methoxy-3,3,14-trimethyl-3,14-dihydro-7H-benzo[α]pyrano[3,2-h]acridin-7-one,
- 6-hydroxy-3,3,14-trimethyl-3,14-dihydro-7H-benzo[α]pyrano[3,2-h]acridin-7-one, and
- 6-hydroxy-3,3-dimethyl-3,14-dihydro-7H-benzo[α]pyrano[3,2-h]acridin-7-one.

17. A method for treating a living animal body, afflicted with cancer, comprising the step of administering to the living animal body, an amount of a compound selected from those of formula (II):

(II)

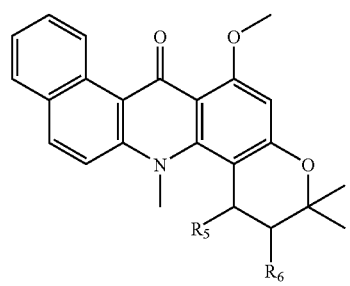

wherein $R_5$ and $R_6$, which may be the same or different, represent, independently of one another, a group selected from:
hydrogen,
$OR_c$, $NR_cR_d$ and $SR_c$, wherein:
  $R_c$ and $R_d$, which may be the same or different, represent, independently of one another, a group selected from hydrogen, linear or branched ($C_1$-$C_6$)alkyl, aryl, aryl-($C_1$-$C_6$)alkyl in which the alkyl moiety is linear or branched, and C(O)—$R_e$, wherein $R_e$ represents a group selected from hydrogen, aryl and $NR'''_aR'''_b$, wherein $R'''_a$ and $R'''_b$, which may be the same or different, represent, independently of one another hydrogen or linear or branched ($C_1$-$C_6$)alkyl, or
  $R'''_a$ and $R'''_b$, together with the nitrogen atom carrying them, form a monocyclic, 5- to 7-membered heterocycle optionally containing in the cyclic system a second hetero atom selected from oxygen and nitrogen,
$W_1$—C($W_2$)—U—V, wherein:
  $W_1$ represents oxygen, sulphur or $NR_c$ wherein $R_c$ is as defined hereinbefore,
  $W_2$ represents oxygen or sulphur,
  U represents linear or branched ($C_1$-$C_8$)alkylene or linear or branched ($C_2$-$C_8$)alkenylene,
  V represents a group selected from:
    hydrogen,
    aryl,
    —$OR_c$, $CO_2R_c$, $COR_c$, $CONR'_aR'_b$, $NR'_aR'_b$, $N(R_c)$—$CO_2R'_c$ and $N(R_c)$—$COR'_c$, wherein $R'_a$, $R'_b$ and $R_c$ are as defined hereinbefore and $R'_c$ represents a group selected from hydrogen, linear or branched ($C_1$-$C_6$)alkyl, aryl and aryl-($C_1$-$C_6$)alkyl in which the alkyl moiety is linear or branched,
  it being understood that U represents a bond when $W_2$ does not represent an oxygen atom and when simultaneously V does not represent a group selected from hydrogen, aryl and $NH_2$,
$W_1$—C($W_2$)—$W_3$-$T_1$, wherein:
  $W_1$ and $W_2$ are as defined hereinbefore,
  $W_3$ represents oxygen, sulphur or $NR_c$, wherein $R_c$ is as defined hereinbefore,
  $T_1$ represents a group selected from:
    hydrogen,
    linear or branched ($C_1$-$C_6$)alkyl,
    linear or branched ($C_2$-$C_6$)alkenyl,
    aryl, aryl-($C_1$-$C_6$)alkyl in which the alkyl moiety is linear or branched,
    linear or branched ($C_1$-$C_6$)alkylene and linear or branched ($C_2$-$C_6$)alkenylene, each being substituted by a group selected from $OR_c$ and $NR'_aR'_b$, wherein $R_c$, $R'_a$ and $R'_b$ are as defined hereinbefore, $W_1$—S(O)$_n$—$W_3$-$T_1$, wherein:
  $W_1$, $W_3$ and $T_1$ are as defined hereinbefore,
  n represents an integer selected from 1 and 2,
$W_1$—S(O)$_n$—U'—V', wherein:
  U' represents linear or branched ($C_1$-$C_8$)alkylene or linear or branched ($C_2$-$C_8$)alkenylene,
  V' represents a group selected from:
    hydrogen,
    aryl,
    $OR_c$, $CO_2R_c$, $COR_c$, $CONR'_aR'_b$, $NR'_aR'_b$, $N(R_c)$—$CO_2R'_c$ and $N(R_c)$—$COR'_c$, wherein $R'_a$, $R'_b$, $R_c$ and $R'_c$ are as defined hereinbefore,
  $W_1$ and n are as defined hereinbefore,
C($W_2$)-$T_1$, wherein $W_2$ and $T_1$ are as defined hereinbefore,
or $R_5$ and $R_6$ together form:

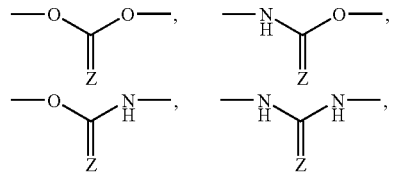

wherein Z represents oxygen or sulphur,
—O—(CH$_2$)$_m$—O—, wherein m represents an integer of from 1 to 4 inclusive,

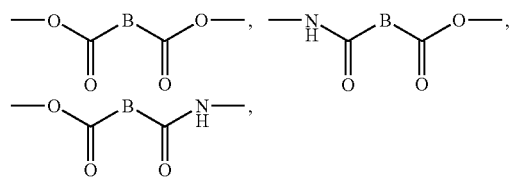

wherein B represents single bond, linear or branched ($C_1$-$C_6$)alkylene or linear or branched ($C_2$-$C_6$)alkenylene,
or $R_5$ and $R_6$, together with the carbon atoms carrying them, form oxirane or aziridine optionally substituted on the nitrogen atom by linear or branched ($C_1$-$C_6$) alkyl,
which is effective for alleviation of cancer.

18. A pharmaceutical composition comprising as active principle an effective amount of a compound of claim 1, together with one or more pharmaceutically acceptable excipients or vehicles.

19. The method of claim 17 wherein the living animal body is a human.

* * * * *